United States Patent [19]

Jojima et al.

[11] 4,052,395

[45] Oct. 4, 1977

[54] AGRICULTURAL FUNGICIDAL COMPOSITIONS CONTAINING 6-(SUBSTITUTED PHENYL)-PYRIDAZINONES AND SAID PYRIDAZINONES

[75] Inventors: Teruomi Jojima, Tokyo; Yukiyoshi Takahi, Yasumachi, both of Japan

[73] Assignee: Sankyo Company Limited, Tokyo, Japan

[21] Appl. No.: 718,589

[22] Filed: Aug. 30, 1976

[30] Foreign Application Priority Data

Sept. 11, 1975  Japan  .............................. 50-110331
Apr. 1, 1976  Japan  .............................. 51-36453

[51] Int. Cl.² .................... A61K 31/50; C07D 237/14; C07D 237/04
[52] U.S. Cl. .............................. 424/250; 260/250 A; 260/515 A; 260/515 R; 260/521 H; 260/518 R; 560/53; 560/138; 560/144
[58] Field of Search .................... 260/250 A; 424/250

[56] References Cited

U.S. PATENT DOCUMENTS

| | | | |
|---|---|---|---|
| 3,824,271 | 7/1974 | Allen, Jr. et al. ............... | 260/250 A |
| 3,825,540 | 7/1974 | Laborit ............................ | 260/250 A |
| 3,891,642 | 6/1975 | Lorenz et al. ................... | 260/250 A |
| 3,975,388 | 8/1976 | Hakim et al. .................... | 260/250 A |

FOREIGN PATENT DOCUMENTS

2,150,436  4/1972  Germany

OTHER PUBLICATIONS

Carran et al. II, J. Med. Chem. 17, pp. 273–281 (1973).
Steck et al. J. Heterocyclic Chem. 11, pp. 755–761 (1921).
Pitarch et al. Chem. Abs. 83, 53193 (1975).

*Primary Examiner*—Donald G. Daus
*Assistant Examiner*—Mark L. Berch
*Attorney, Agent, or Firm*—Flynn & Frishauf

[57] ABSTRACT

Agricultural fungicidal compositions containing as an active ingredient one or more of 6-(substitutedphenyl)-3(2H)-pyridazinone compounds, salts thereof and 6-(substituted-phenyl)-4,5-dihydro-3(2H)-pyridazinone compounds, as well as new pyridazinone compounds having fungicidal activities.

24 Claims, No Drawings

AGRICULTURAL FUNGICIDAL COMPOSITIONS CONTAINING 6-(SUBSTITUTED PHENYL)-PYRIDAZINONES AND SAID PYRIDAZINONES

This invention relates to the use of pyradazinone derivatives as agricultural fungicides and a certain group of new pyridazinone derivatives.

More particularly, it is concerned with an agricultural fungicidal composition which comprises as an active ingredient a compound having the formula

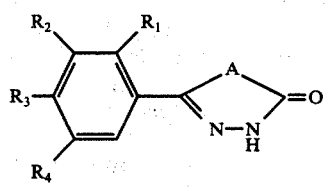
(I)

wherein
- $R_1$ is hydrogen atom, hydroxy group, a group of the formula -O-CO-$R_5$ in which $R_5$ is an alkyl group of 1-5 carbon atoms or a group of the formula -O-SO$_2$-$R_6$ in which $R_6$ is a phenyl group optionally substituted with a halogen or an alkyl group of 1-3 carbon atoms;
- $R_2$ and $R_4$ may be the same or different and each represents a halogen atom or one of $R_2$ and $R_4$ is a halogen atom and the other is hydrogen atom;
- $R_3$ is hydrogen atom, an alkyl group of 1-6 carbon atoms, an alkoxy group of 1-6 carbon atoms, an alkenyloxy group of 3-5 carbon atoms, an alkynyloxy group of 3-4 carbon atoms, amino group, hydroxy group, a halogen atom, a group of the formula -O-CO-$R_5$ in which $R_5$ is as defined above or a group of the formula -O-SO$_2$-$R_6$ in which $R_6$ is as defined above; and
- A is a group -CH$_2$-CH$_2$- or -CH=CH- or a salt thereof where A is the group -CH=CH-, as well as with some new pyradazinone derivatives having the formula

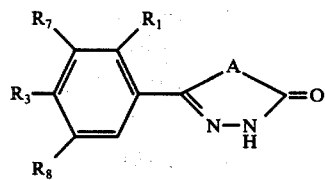
(II)

wherein
- $R_1$ is hydrogen atom, hydroxy group, a group of the formula -O-CO-$R_5$ in which $R_5$ is an alkyl group of 1-5 carbon atoms or a group of the formula -O-SO$_2$-$R_6$ in which $R_6$ is a phenyl group optionally substituted with a halogen atom or an alkyl group of 1-3 carbon atoms;
- $R_7$ and $R_8$ may be the same or different and each represents a halogen atom or one of $R_7$ and $R_8$ is a halogen atom and the other is hydrogen atom; and each represents a halogen atom;
- $R_3$ is hydrogen atom, an alkyl group of 1-6 carbon atoms, an alkoxy group of 1-6 carbon atoms, an alkenyloxy group of 3-5 carbon atoms, an alkynyloxy group of 3-4 carbon atoms, amino group, hydroxy group, a halogen atom, a group of the formula -O-CO-$R_5$ in which $R_5$ is as defined above or a group of the formula -O-SO$_2$-$R_6$ in which $R_6$ is as defined above; and
- A is a group -CH$_2$-CH$_2$- or -CH=CH- or a salt thereof where A is the group -CH=CH-, provided that when $R_3$ is hydrogen atom, said alkyl group, said alkenyloxy group, said alkynyloxy group, amino group, said group -O-CO-$R_5$ or said group -O-SO$_2$-$R_6$, one of $R_7$ and $R_8$ is a halogen atom and the other is hydrogen atom.

The compounds of the above formula (I) wherein A is the group -CH=CH- may be present in the form of the tautomerism as shown below.

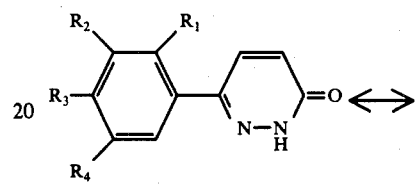

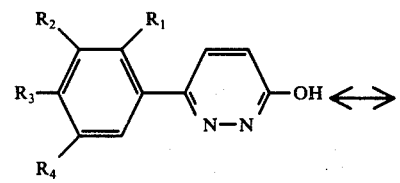

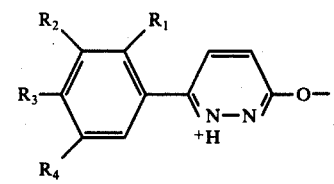

In the formulae, $R_1$, $R_2$, $R_3$ and $R_4$ are as defined above. It is, of course, to be noted that the same tautomerism as shown above may be observed with respect to the compounds (II).

In the above formula (I), chlorine, bromine, fluorine and iodine may be mentioned as examples of the halogen atoms in $R_2$, $R_3$ and $R_4$, preferably chlorine, fluorine and bromine being mentioned.

As an example of the alkyl group in $R_3$ may be mentioned a straight or branched lower alkyl group having 1 to 6 carbon atoms such as methyl, ethyl, n-propyl, isopropyl, n-butyl, isobutyl, sec-butyl, tert-butyl, n-amyl, isoamyl, sec-amyl or n-hexyl, preferably a lower alkyl group of 1 to 2 carbon atoms.

As an example of the alkoxy group in $R_3$ may be mentioned a straight or branched lower alkoxy group having 1 to 6 carbon atoms such as methoxy, ethoxy, n-propoxy, isopropoxy, n-butoxy, isobutoxy, sec-butoxy, tert-butoxy, n-amyloxy, isoamyloxy, sec-amyloxy or n-hexyloxy, preferably an alkoxy group of 1 to 2 carbon atoms.

As an example of the $R_6$ in the group -O-SO$_2$-$R_6$ may be mentioned phenyl, o-, m- or p-chlorophenyl, p-bromophenyl, 2,4-dichlorophenyl, o-, m- or p-tolyl, 4-ethylphenyl or 2-n-propylphenyl, preferably p-tolyl.

As an example of the alkenyloxy group in $R_3$ may be mentioned allyloxy, 2-butenyloxy, 1-methyl-2-propenyloxy, 2-methyl-2-propenyloxy, 3-butenyloxy or 2-pentenyloxy, preferably an alkenyloxy group of 3 to 4 carbon atoms.

As an example of the alkynyloxy group in $R_3$ may be mentioned 2-propynyloxy, 1-methyl-2-propynyloxy, 2-butynyloxy or 3-butynyloxy, preferably 2-propynyloxy.

The salts of the compounds of the above formula (I) can be formed only when A is the group -CH=CH- and included within the purview of this invention. A salt as used herein is meant to include an acid addition salt such as that with a mineral acid, e.g., hydrochloric acid, sulfuric acid, hydrobromic acid or phosphoric acid; an adduct with an alkyl isocyanate, e.g., methyl isocyanate; an alkali metal salt, e.g., sodium, potassium or lithium salt; an alkaline earth metal salt, e.g., calcium or magnesium salt; a salt with a monovalent to trivalent metal ion, e.g., aluminum or copper ion; and a salt with a complex ion.

In the agricultural chemicals field, there were previously proposed various types of compounds as fungicides and many of them have been nowadays practically utilized as active ingredients in fungicidal compositions. However, there is a continuous demand for much more effective fungicidal compounds in the art.

As a result of our extensive studies on pyridazinone derivatives and their biological activity, we have unexpectedly found that the pyridazinone derivatives having the above formula (I) and the specific salts thereof show prominent fungicidal activities and also that the pyridazinone derivatives having the above formula (II) are new substances which are useful as agricultural fungicides.

With regard to the prior art found during our studies, there are pointed out the following facts.

1. U.S. Pat. No. 2,624,730 discloses that 6-(4-halogeno- or 3,4-dihalogenophenyl)-3(2H)-pyridazinones are useful only as an amoebacide.
2. J. Heterocyclic. Chem., 11, 755 (1974) discloses that 6-(4-chloro-3-methylphenyl)-3(2H)pyridazinone, 6-(3-bromo-4-methoxyphenyl)-3(2H)pyridazinone and 6-(4-chloro-3-nitrophenyl)-3(2H)pyridazinone, 6-(4-methoxyphenyl)-3(2H)pyridazinone, 6-(4-methoxyphenyl)-4,5-dihydro-3(2H)pyridazinone, and 6-(4-chloro-3-methylphenyl)-4,5-dihydro-3(2H)pyridazinone are employable only as antiprotozoal agents.
3. French Patent No. 1,507,475 discloses that 6-(4-aminophenyl)-4,5-dihydro-3(2H)-pyridazinone is employable as an intermediate for the synthesis of medicines and dyestuffs.
4. Japanese Patent Application Laid-Open Specification No. 93984/1975 discloses that 6-(3-chloro-4-hydroxyphenyl)-4,5-dihydro-3(2H)-pyridazinone is useful as an intermediate for the synthesis of medicines.
5. Japanese Patent Publication No. 12740/1969 discloses that 6-(4-aminophenyl)-3(2H)-pyridazinone is employable as an intermediate for the synthesis of dyestuffs.

It is, accordingly, a primary object of this invention to provide an effective agricultural fungicidal composition containing a pyridazinone derivative (I).

Another object of this invention is to provide a certain group of new pyridazinone derivatives (II) having fungicidal activities.

Other objects and advantages of this invention will become apparent from the description given below.

In one aspect of this invention, there is provided an agricultural fungicidal composition which comprises as an active ingredient a pyridazinone compound of the formula (I) or a salt thereof and an agriculturally acceptable carrier.

Among the pyridazinone compounds of the formula (I), a preferable group includes those wherein A. $R_1$ is hydrogen atom or hydroxy group, particularly hydrogen atom, $R_2$ and $R_4$ may be the same or different and each represents a chlorine atom, fluorine atom or bromine atom and $R_3$ is hydrogen atom, amino group, an alkyl group of 1 or 2 carbon atoms, particularly methyl group, an alkoxy group of 1 or 2 carbon atoms, particularly methoxy group, or an alkenyloxy group of 3 or 4 carbon atoms, particularly allyloxy group or B. $R_1$ and $R_4$ are hydrogen atoms; and $R_2$ and $R_3$ may be the same or different and each represents a chlorine atom, fluorine atom or bromine atom or $R_2$ is a chlorine atom or bromine atom and $R_3$ is a hydrogen atom or an alkyl group of 1 or 2 carbon atoms. Also, the corresponding salts are similarly preferable.

Further, as a more preferable group may be mentioned those pyridazinone compounds (I) wherein $R_1$ is a hydrogen atom, $R_2$ and $R_4$ may be the same or different and each represents a chlorine atom, fluorine atom or bromine atom and $R_3$ is an alkyl group of 1 or 2 carbon atoms or an alkoxy group of 1 or 2 carbon atoms.

The following is a list of representative examples of the pyridazinone derivatives of the formula (I). The numbers appended to the compounds in this list will be frequently used hereinafter to identify the same compounds.

| Compound No. | Chemical Name |
|---|---|
| 1. | 6-(3,4-dichlorophenyl)-3(2H)pyridazinone |
| 2. | 6-(3,4,5-trichlorophenyl)-3(2H)pyridazinone |
| 3. | 6-(3,4-dichloro-5-bromophenyl)-3(2H)-pyridazinone |
| 4. | 6-(3-chloro-4-methylphenyl)-3(2H)pyridazinone |
| 5. | 6-(3-bromo-4-methylphenyl)-3(2H)pyridazinone |
| 6. | 6-(3-chloro-4-isopropylphenyl)-3(2H)-pyridazinone |
| 7. | 6-(3,5-dichloro-4-methylphenyl)-3(2H)-pyridazinone |
| 8. | 6-(3,5-dibromo-4-methylphenyl)-3(2H)-pyridazinone |
| 9. | 6-(3,5-diiodo-4-methylphenyl)-3(2H)-pyridazinone |
| 10. | 6-(3,5-dichloro-4-ethylphenyl)-3(2H)-pyridazinone |
| 11. | 6-(3,5-dibromo-4-ethylphenyl)-3(2H)-pyridazinone |
| 12. | 6-(3,5-dichloro-4-n-propylphenyl)-3(2H)-pyridazinone |
| 13. | 6-(3,5-dibromo-4-n-propylphenyl)-3(2H)-pyridazinone |
| 14. | 6-(3,5-dichloro-4-n-butylphenyl)-3(2H)-pyridazinone |
| 15. | 6-(3,5-dichloro-4-sec-butylphenyl)-3(2H)-pyridazinone |
| 16 | 6-(3,5-dichloro-4-tert-butylphenyl)-3(2H)-pyridazinone |
| 17. | 6-(3,5-dichloro-5-n-pentylphenyl)-3(2H)-pyridazinone |
| 18. | 6-(3,5-dichloro-4-sec-amylphenyl)-3(2H)-pyridazinone |
| 19. | 6-(3,5-dichloro-4-n-hexylphenyl)-3(2H)-pyridazinone |
| 20. | 6-(3,5-dibromo-4-chloro-2-hydroxyphenyl)-3(2H)pyridazinone |
| 21. | 6-(3,5-dibromo-4-methyl-2-hydroxyphenyl)-3(2H)pyridazinone |
| 22. | 6-(3,5-dichloro-4-methyl-2-hydroxyphenyl)-3(2H)pyridazinone |
| 23. | 6-(3,5-dibromo-4-ethyl-2-hydroxyphenyl)-3(2H)pyridazinone |
| 24. | 6-(3,5-dibromo-4-tert-butyl-2-hydroxyphenyl)-3(2H)pyridazinone |
| 25. | 6-(5-chloro-4-methyl-2-hydroxyphenyl)-3(2H)-pyridazinone |

| Compound No. | Chemical Name |
|---|---|
| 26. | 6-(3,5-dichloro-4-hydroxyphenyl)-3(2H)-pyridazinone |
| 27. | 6-(3,5-dibromo-4-hydroxyphenyl)-3(2H)-pyridazinone |
| 28. | 6-(3-bromo-5-chloro-4-methyl-2-hydroxyphenyl)-3(2H)pyridazinone |
| 29. | 6-(3-chloro-4-ethylphenyl)-3(2H)pyridazinone |
| 30. | 6-(3-bromo-5-chloro-4-methylphenyl)-3(2H)-pyridazinone |
| 31. | 6-(3-bromophenyl)-3(2H)pyridazinone |
| 32. | 6-(3-chlorophenyl)-3(2H)pyridazinone |
| 33. | 6-(3-chloro-4-methoxyphenyl)-3(2H)pyridazinone |
| 34. | 6-(3,5-dichloro-4-methyoxyphenyl)-3(2H)-pyridazinone |
| 35. | 6-(3-chloro-4-aminophenyl)-3(2H)pyridazinone |
| 36. | 6-(3-bromo-4-aminophenyl)-3(2H)pyridazinone |
| 37. | 6-(3,5-dibromo-4-aminophenyl)-3(2H)pyridazinone |
| 38. | 6-(3,5-dibromophenyl)-3(2H)pyridazinone |
| 39. | 6-(3-bromo-5-chloro-2-hydroxyphenyl)-3(2H)-pyridazinone |
| 40. | 6-(3,5-dichloro-4-methoxy-2-hydroxyphenyl)-3(2H)pyridazinone |
| 41. | 6-(3,5-dibromo-4-ethoxyphenyl)-3(2H)-pyridazinone |
| 42. | 6-(5-chloro-2-hydroxyphenyl)-3(2H)-pyridazinone |
| 43. | 6-(3,5-dichloro-2-hydroxyphenyl)-3(2H)-pyridazinone |
| 44. | 6-(3,5-dichloro-4-aminophenyl)-3(2H)-pyridazinone |
| 45. | 6-(3,5-dichloro-4-ethoxyphenyl)-3(2H)-pyridazinone |
| 46. | 6-(3,5-dibromo-4-methoxyphenyl)-3(2H)-pyridazinone |
| 47. | 6-(3-chloro-5-bromo-4-aminophenyl)-3(2H)-pyridazinone |
| 48. | 6-(3-chloro-5-bromo-4-methoxyphenyl)-3(2H)-pyridazinone |
| 49. | 6-(3-chloro-5-bromo-4-ethoxyphenyl)-3(2H)-pyridazinone |
| 50. | 6-(3,5-diiodo-4-hydroxyphenyl)-3(2H)-pyridazinone |
| 51. | 6-(3-chloro-4-bromophenyl)-3(2H)pyridazinone |
| 52. | 6-(3,5-dichloro-4-isopropylphenyl)-3(2H)-pyridazinone |
| 53. | 6-(3,5-dibromo-4-isopropylphenyl)-3(2H)-pyridazinone |
| 54. | 6-(3-chloro-2-hydroxyphenyl)-3(2H)pyridazinone |
| 55. | 6-(3-chloro-4-methyl-2-hydroxyphenyl)-3(2H)-pyridazinone |
| 56. | 6-(3,5-dichloro-2,4-dihydroxyphenyl)-3(2H)-pyridazinone |
| 57. | 6-(3,4-dichloro-2-hydroxyphenyl)-3(2H)-pyridazinone |
| 58. | 6-(5-chloro-4-methoxy-2-hydroxyphenyl)-3(2H)pyridazinone |
| 59. | 6-(5-bromo-2,4-dihydroxyphenyl)-3(2H)-pyridazinone |
| 60. | 6-(4,5-dichloro-2-hydroxyphenyl)-3(2H)-pyridazinone |
| 61. | 6-(3,4-dibromophenyl)-3(2H)pyridazinone |
| 62. | 6-(3-chloro-4-fluorophenyl)-3(2H)pyridazinone |
| 63. | 6-(3-bromo-4-chlorophenyl)-3(2H)pyridazinone |
| 64. | 6-(3-bromo-4-fluorophenyl)-3(2H)pyridazinone |
| 65. | 6-(3-iodophenyl)-3(2H)pyridazinone |
| 66. | 6-(3,4-dichlorophenyl)-3(2H)pyridazinone methylisocyanate |
| 67. | 6-(3,5-dichloro-4-methylphenyl)-3(2H)-pyridazinone methylisocyanate |
| 68. | 6-(3-chloro-4-methylphenyl)-3(2H)pyridazinone methylisocyanate |
| 69. | 6-(3-bromo-4-methylphenyl)-3(2H)pyridazinone methylisocyanate |
| 70. | 6-(3-chlorophenyl)-3(2H)pyridazinone hydrobromide |
| 71. | 6-(3-bromophenyl)-3(2H)pyridazinone hydrobromide |
| 72. | 6-(3,5-dichloro-4-hydroxyphenyl)-3(2H)-pyridazinone methylisocyanate |
| 73. | 6-(3,5-dibromo-4-n-hexylphenyl)-3(2H)-pyridazinone |
| 74. | 6-(3,5-dichlorophenyl)-3(2H)-pyridazinone |
| 75. | 6-(4-allyloxy-3,5-dichlorophenyl)-3(2H)-pyridazinone |
| 76. | 6-(3,5-dichloro-4-(2-propynyloxy)phenyl)-3(2H)pyridazinone |
| 77. | 6-(3,5-dichloro-4-bromophenyl)-3(2H)-pyridazinone |
| 78. | 6-(2-acetoxy-3,5-dibromo-4-methylphenyl)-3(2H)pyridazinone |
| 79. | 6-(2-acetoxy-3-bromo-5-chloro-4-methylphenyl)-3(2H)pyridazinone |
| 80. | 6-(2-acetoxy-3,5-dichloro-4-methylphenyl)-3(2H)pyridazinone |
| 81. | 6-(3,5-dibromo-2-butyryloxy-4-methylphenyl)-3(2H)pyridazinone |
| 82. | 6-(4-acetoxy-3,5-dichlorophenyl)-3(2H)-pyridazinone |
| 83. | 6-(3,5-dichloro-4-p-toluenesulfonyloxyphenyl)-3(2H)pyridazinone |
| 84. | 6-(3,5-dibromo-4-methyl-2-p-toluenesulfonyloxyphenyl)-3(2H)pyridazinone |
| 85. | 6-(3,5-dibromo-2-p-chlorobenzenesulfonyloxy-4-methylphenyl)-3(2H)pyridazinone |
| 86. | 6-(3-chloro-5-fluoro-4-methylphenyl)-3(2H)pyridazinone |
| 87. | 6-(3,4-dichlorophenyl)-4,5-dihydro-3(2H)pyridazinone |
| 88. | 6-(3,4,5-trichlorophenyl)-4,5-dihydro-3(2H)pyridazinone |
| 89. | 6-(3,4-dichloro-5-bromophenyl)-4,5-dihydro-3(2H)pyridazinone |
| 90. | 6-(3-chloro-4-methylphenyl)-4,5-dihydro-3(2H)pyridazinone |
| 91. | 6-(3-bromo-4-methylphenyl)-4,5-dihydro-3(2H)pyridazinone |
| 92. | 6-(3-chloro-4-isopropylphenyl)-4,5-dihydro-3(2H)pyridazinone |
| 93. | 6-(3,5-dichloro-4-methylphenyl)-4,5-dihydro-3(2H)pyridazinone |
| 94. | 6-(3,5-dibromo-4-methylphenyl)-4,5-dihydro-3(2H)pyridazinone |
| 95. | 6-(3,5-diiodo-4-methylphenyl)-4,5-dihydro-3(2H)pyridazinone |
| 96. | 6-(3,5-dichloro-4-ethylphenyl)-4,5-dihydro-3(2H)pyridazinone |
| 97. | 6-(3,5-dibromo-4-ethylphenyl)-4,5-dihydro-3(2H)pyridazinone |
| 98. | 6-(3,5-dichloro-4-n-propylphenyl)-4,5-dihydro-3(2H)pyridazinone |
| 99. | 6-(3,5-dibromo-4-n-propylphenyl)-4,5-dihydro-3(2H)pyridazinone |
| 100. | 6-(3,5-dichloro-4-n-butylphenyl)-4,5-dihydro-3(2H)pyridazinone |
| 101. | 6-(3,5-dichloro-4-sec-butylphenyl)-4,5-dihydro-3(2H)pyridazinone |
| 102. | 6-(3,5-dichloro-4-tert-butylphenyl)-4,5-dihydro-3(2H)pyridazinone |
| 103. | 6-(3,5-dichloro-4-n-pentylphenyl)-4,5-dihydro-3(2H)pyridazinone |
| 104. | 6-(3,5-dichloro-4-sec-amylphenyl)-4,5-dihydro-3(2H)pyridazinone |
| 105. | 6-(3,5-dichloro-4-n-hexylphenyl)-4,5-dihydro-3(2H)pyridazinone |
| 106. | 6-(3,5-dibromo-4-chloro-2-hydroxyphenyl)-4,5-dihydro-3(2H)pyridazinone |
| 107. | 6-(3,5-dibromo-4-methyl-2-hydroxyphenyl)-4,5-dihydro-3(2H)pyridazinone |
| 108. | 6-(3,5-dichloro-4-methyl-2-hydroxyphenyl)-4,5-dihydro-3(2H)pyridazinone |
| 109. | 6-(3,5-dibromo-4-ethyl-2-hydroxyphenyl)-4,5-dihydro-3(2H)pyridazinone |
| 110. | 6-(3,5-dibromo-4-tert-butyl-2-hydroxyphenyl)-4,5-dihydro-3(2H)pyridazinone |
| 111. | 6-(5-chloro-4-methyl-2-hydroxyphenyl)-4,5-dihydro-3(2H)pyridazinone |
| 112. | 6-(3,5-dichloro-4-hydroxyphenyl)-4,5-dihydro-3(2H)pyridazinone |
| 113. | 6-(3,5-dibromo-4-hydroxyphenyl)-4,5-dihydro-3(2H)pyridazinone |
| 114. | 6-(3-bromo-5-chloro-4-methyl-2-hydroxyphenyl)-4,5-dihydro-3(2H)pyridazinone |
| 115. | 6-(3-chloro-4-ethylphenyl)-4,5-dihydro-3(2H)pyridazinone |
| 116. | 6-(3-bromo-5-chloro-4-methylphenyl)-4,5-dihydro-3(2H)pyridazinone |
| 117. | 6-(3-bromophenyl)-4,5-dihydro-3(2H)pyridazinone |
| 118. | 6-(3-chlorophenyl)-4,5-dihydro-3(2H)pyridazinone |
| 119. | 6-(3-chloro-4-methoxyphenyl)-4,5-dihydro-3(2H)pyridazinone |
| 120. | 6-(3,5-dichloro-4-methoxyphenyl)-4,5-dihydro-3(2H)pyridazinone |
| 121. | 6-(3-chloro-4-aminophenyl)-4,5-dihydro-3(2H)pyridazinone |
| 122. | 6-(3-bromo-4-aminophenyl)-4,5-dihydro-3(2H)pyridazinone |
| 123. | 6-(3,5-dibromo-4-aminophenyl)-4,5-dihydro-3(2H)pyridazinone |
| 124. | 6-(3,5-dibromophenyl)-4,5-dihydro-3(2H)- |

| Compound No. | Chemical Name |
|---|---|
| | pyridazinone |
| 125. | 6-(3-bromo-5-chloro-2-hydroxyphenyl)-4,5-dihydro-3(2H)pyridazinone |
| 126. | 6-(3,5-dichloro-4-methoxy-2-hydroxyphenyl)-4,5-dihydro-3(2H)pyridazinone |
| 127. | 6-(3,5-dibromo-4-ethoxyphenyl)-4,5-dihydro-3(2H)pyridazinone |
| 128. | 6-(5-chloro-2-hydroxyphenyl)-4,5-dihydro-3(2H)pyridazinone |
| 129. | 6-(3,5-dichloro-2-hydroxyphenyl)-4,5-dihydro-3(2H)pyridazinone |
| 130. | 6-(3,5-dichloro-4-aminophenyl)-4,5-dihydro-3(2H)pyridazinone |
| 131. | 6-(3,5-dichloro-4-ethoxyphenyl)-4,5-dihydro-3(2H)pyridazinone |
| 132. | 6-(3,5-dibromo-4-methoxyphenyl)-4,5-dihydro-3(2H)pyridazinone |
| 133. | 6-(3-chloro-5-bromo-4-aminophenyl)-4,5-dihydro-3(2H)pyridazinone |
| 134. | 6-(3-chloro-5-bromo-4-methoxyphenyl)-4,5-dihydro-3(2H)pyridazinone |
| 135. | 6-(3-chloro-5-bromo-4-ethoxyphenyl)-4,5-dihydro-3(2H)pyridazinone |
| 136. | 6-(3,5-diiodo-4-hydroxyphenyl)-4,5-dihydro-3(2H)pyridazinone |
| 137. | 6-(3-chloro-4-bromophenyl)-4,5-dihydro-3(2H)pyridazinone |
| 138. | 6-(3,5-dichloro-4-isopropylphenyl)-4,5-dihydro-3(2H)pyridazinone |
| 139. | 6-(3-chloro-4-fluorophenyl)-4,5-dihydro-3(2H)pyridazinone |
| 140. | 6-(3,5-dibromo-4-n-hexylphenyl)-4,5-dihydro-3(2H)pyridazinone |
| 141. | 6-(3,5-dichloro-2,4-dihydroxyphenyl)-4,5-dihydro-3(2H)pyridazinone |
| 142. | 6-(5-bromo-2,4-dihydroxyphenyl)-4,5-dihydro-3(2H)pyridazinone |
| 143. | 6-(4,5-dichloro-2-hydroxyphenyl)-4,5-dihydro-3(2H)pyridazinone |
| 144. | 6-(3,5-dichlorophenyl)-4,5-dihydro-3(2H)pyridazinone |
| 145. | 6-(3-iodophenyl)-4,5-dihydro-3(2H)pyridazinone |
| 146. | 6-(3,5-dichloro-4-allyloxyphenyl)-4,5-dihydro-3(2H)pyridazinone |
| 147. | 6-(3,5-dichloro-4-n-propoxyphenyl)-4,5-dihydro-3(2H)pyridazinone |
| 148. | 6-(3,5-dichloro-4-(2-propynyloxy)phenyl)4,5-dihydro-3(2H)pyridazinone |
| 149. | 6-(3,5-diiodo-4-methoxyphenyl)-4,5-dihydro-3(2H)pyridazinone |
| 150. | 6-(3,5-dichloro-4-fluorophenyl)-4,5-dihydro-3(2H)pyridazinone |
| 151. | 6-(2-acetoxy-3,5-dichloro-4-methylphenyl)-4,5-dihydro-3(2H)pyridazinone |
| 152. | 6-(3,5-dichloro-4-p-toluenesulfonyloxyphenyl)-4,5-dihydro-3(2H)pyridazinone |
| 153. | 6-(3,5-dichlorophenyl-4-acetoxyphenyl)-4,5-dihydro-3(2H)pyridazinone |
| 154. | 6-(3,5-dibromo-4-methyl-2-p-toluenesulfonyloxyphenyl)-4,5-dihydro-3(2H)pyridazinone |
| 155. | 6-(3-fluorophenyl)-4,5-dihydro-3(2H)pyridazinone |
| 156. | 6-(3-fluoro-4-methoxyphenyl)-4,5-dihydro-3(2H)pyridazinone |
| 157. | 6-(3,4-difluorophenyl)-4,5-dihydro-3(2H)-pyridazinone |
| 158. | 6-(3,4-dibromophenyl)-4,5-dihydro-3(2H)-pyridazinone |
| 159. | 6-(3-chloro-5-fluoro-4-methylphenyl)-4,5-dihydro-3(2H)pyridazinone |
| 160. | 6-(3-bromo-4-chlorophenyl)-4,5-dihydro-3(2H)pyridazinone |
| 161. | 6-(3-bromo-4-fluorophenyl)-4,5-dihydro-3(2H)pyridazinone |
| 162. | 6-(4-bromo-3,5-dichlorophenyl)-4,5-dihydro-3(2H)pyridazinone |

Of the above-listed pyridazinone compounds, there can be mentioned, particularly in view of the fungicidal activity against pathogenic fungi Rhizoctonia, as a preferable group those compounds of Compound Nos. 1, 4, 5, 7, 8, 30, 31, 32, 34, 87, 117 and 120.

Also, there can be mentioned, particularly in view of the effect on sheath blight of rice plants, as a preferable group those compounds of Compound Nos. 1, 2, 4, 5, 6, 7, 8, 10, 20, 21, 28, 30, 34, 37, 61, 62, 63, 64, 66, 67, 68, 69 and 120 and the most preferable group includes those compounds of Compound Nos. 1, 7, 8, 30, 34 and 62.

Of the above-listed compounds, those having Compound Nos. 1 and 87 are known per se, but other compounds are new substances.

The compounds having the above formula (I) which may be employed as active ingredients in this invention can be illustrated, for example, by the processes and by the following reaction schemata.

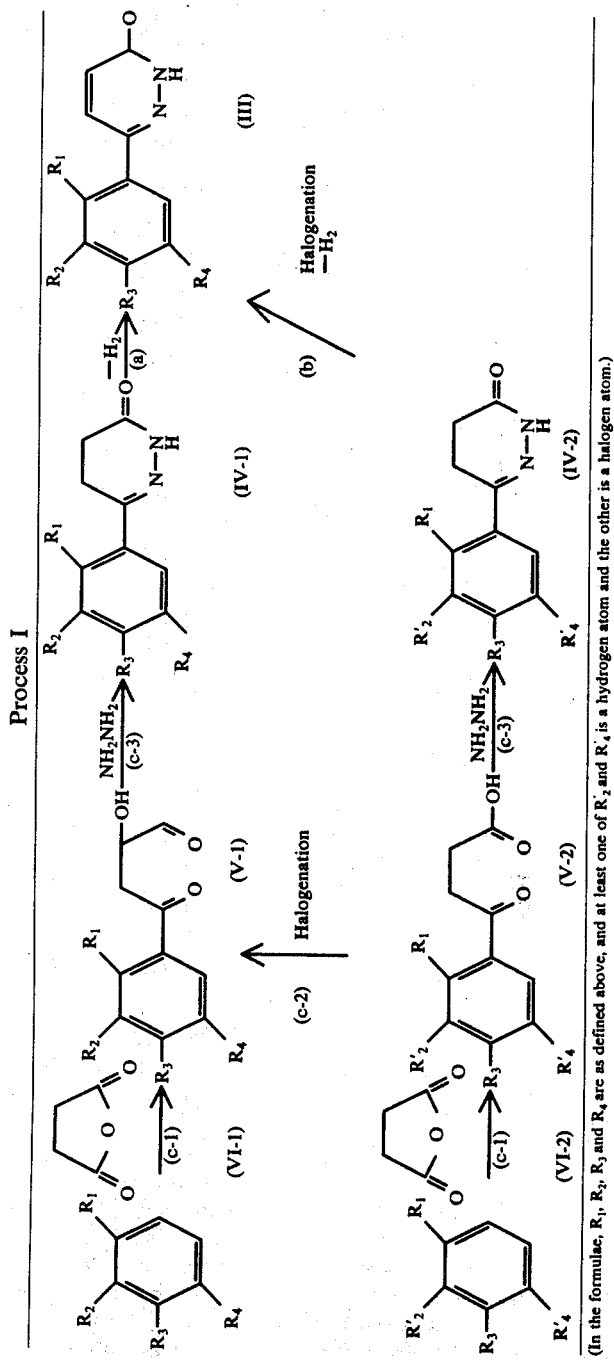

Step a — The compounds having the formula (III) are prepared by dehydrogenation of the 6-substituted phenyl-4,5-dihydro-3(2H)pyridazinones represented by the formula (IV-1) according to the method disclosed in J. Am. Chem. Soc., 75, 1117 (1953).

This reaction can be conducted in the presence of a dehydrogenating agent. The dehydrogenating agent which may be employed may be, for example, bromine, chlorine, nitric acid, sodium hypochlorite, sodium chlorate, selenium dioxide or sodium m-nitrobenzenesulfonate, particularly bromine.

The reaction may be preferably conducted in the presence of a solvent. As the solvent which may be employed, there is no particular limitation if it does not participate in the present reaction; for example, an organic acid, e.g., acetic acid, propionic acid or butyric acid, an alcohol, e.g., methanol, ethanol, n-propanol, isopropanol or n-butanol, a cyclic ether, e.g., dioxane or tetrahydrofuran, a ketone, e.g., acetone or methyl ethyl ketone or a mixed solvent thereof with water may be employed.

It is particularly preferable to employ bromine as a dehydrogenating agent and acetic acid as a solvent, and the reaction temperature in this case is desirably about 50° C or higher, preferably temperatures around a reflux temperature of the solvent. The reaction period may vary depending upon the reaction temperature and sort of reagent employed, but usually about 1 to 10 hours.

When sodium m-nitrobenzenesulfonate is employed as a dehydrogenating agent, the reaction may conveniently be carried out in the way disclosed in Japanese Patent Publication 12740/1969 specification. In that case, a solvent may preferably be water or a mixture of water with an alcohol such as ethanol, isopropanol or n-butanol, and the reaction is preferably carried out in the presence of an inorganic base such as sodium hydroxide or potassium hydroxide.

After completion of the reaction, the desired product can be recovered from the reaction mixture in a conventional manner. Step b — The compounds having the formula (III) are also prepared by direct halogenation of the compounds having the formula (IV-2) wherein at least one hydrogen atom is located at the 3- and 5-positions of the benzene ring.

This reaction may be performed by heating the compounds of the formula (IV-2) with the halogenating agent in an inert solvent to simultaneously accomplish both dehydrogenation of the dihydropyridazine nucleus and halogenation at the 3- and/or 5-position of the benzene nucleus and, in particular, the reaction can produce, starting from the compounds of the formula (IV-2) wherein $R_1$ is hydroxy group and both $R'_2$ and $R'_4$ are hydrogen atoms, the corresponding compounds of the formula (III).

As the halogenating agent which may be employed in this reaction, may be mentioned chlorine, bromine, iodine, iodine monochloride and the like. In particular, bromine or chlorine may be preferably employed. As the reaction solvent, there may be employed an organic acid such as acetic acid, propionic acid, butyric acid or the like or a mixture thereof with water, acetic acid being preferable. The reaction temperature is usually not lower than 50° C., a reflux temperature of the solvent employed being preferable. The reaction period of time may vary depending upon the reaction temperature, a sort of the reagent employed, but it is usually about 1 to 10 hours. Step c — The starting material of the formula (IV-1) or (IV-2) can be prepared by the following processes which are well known per se. More specifically, Step c-1 — Substituted benzoylpropionic acids of the formula (V-1) or (V-2) can be prepared by, what is called, Friedel-Crafts reaction, namely, by reaction of substituted benzenes of the formula (VI-1) or (VI-2) and succinic anhydride with a Lewis acid.

This process is conducted according to the method described in "Organic Reactions", 5, 229 (1949), edited by Roger Adams, published by the John Willey and Sons. Co., Ltd. As the Lewis acid which may be employed in the reaction, there may be mentioned, for example, aluminum chloride, ferric chloride, titanium tetrachloride, zinc chloride, stannic chloride or the like, and aluminum chloride is particularly preferable. A molar ratio of the compound of the formula (VI-1) or (VI-2) to the Lewis acid is 1:1 to 1:4, 1:2 to 1:2.5 being preferable. It is also preferable to conduct this reaction in an inert organic solvent. The solvent, which may be employed in this connection, may be carbon disulfide; an aromatic hydrocarbon such as nitrobenzene or dichlorobenzene; a halogenated aliphatic hydrocarbon such as dichloromethane, dichloroethane or tetrachloroethane, or the like. The reaction may be also effected in the absence of the solvent by the use of a large excess of the aforesaid substituted benzene (VI-1) or (VI-2). Step c-2 — The compounds having the formula (V-1) can also be prepared by reaction of 3-benzoylpropionic acids of the formula (V-2), wherein at least one hydrogen atom is located at the 3- and 5-positions of the benzene ring, with a halogenating agent in the presence of a Lewis acid.

This process can be effected according to the method described in Arzneimittel Forschung, 24, 1360 (1974).

As the halogenating agent which may be employed, there may be mentioned chlorine, bromine, iodine, iodine monochloride, sulfuryl chloride or sulfuryl bromide.

With respect to the Lewis acid and reaction solvent, there may be mentioned those which are disclosed in the aforesaid process (c-1).

In the halogenation, for instance, a benzoylpropionic acid of the formula (V-2) wherein the 3- and 5-positions of the benzene ring are both occupied by hydrogen atoms may be firstly chlorinated at the 3-position and further brominated at the 5-position. Alternatively, it may be firstly brominated at the 3-position and further chlorinated at the 5-position. Step c-3 — Then, the 6-substituted phenyl-4,5-dihydro-3(2H)pyridazinones of the formula (IV-1) or (IV-2) can be prepared by reaction of the 3-substituted benzoylpropionic acids of the formula (V-1) or (V-2) with a hydrazine.

This process is effected according to the method described in J.A.C.S., 75, 1117 (1953). As the hydrazine which may be employed in this reaction, there may be mentioned hydrazine hydrate, hydrazine hydrochloride and hydrazine sulfate. This reaction may also be preferably conducted in the presence of a solvent. As the solvent which may be employed, there is no particular limitation if it does not participate in the present reaction: for example, an alcohol such as methanol, ethanol, n-propanol, isopropanol or n-butanol; a cyclic ether such as tetrahydrofuran or dioxane; an organic acid such as acetic acid or propionic acid; a halogenated hydrocarbon such as dichloromethane or dichloroethane; and water. Particularly, the alcohol can be preferably employed. Reaction temperature is room temperature or higher than that, preferably around a reflux temperature of the solvent employed. Reaction period of time may vary depending upon the reaction temperature and sort of reagent employed, but it is usually about 0.5 – 10 hours.

The compounds of the formula (IV-1) or (IV-2) may also be prepared by esterification (to lower alkyl ester) of the 3-substituted benzoylpropionic acids of the formula (V-1) or (V-2) or conversion of said acids to a corresponding functional derivatives such as amides (for example, an amide or a lower alkylamide) in a conventional manner and subsequent reaction of these esters or amides with a hydrazine in the same manner as mentioned above.

In addition, a compound of the formula (IV-1) can as such be directly converted to the desired compound of the formula (III) by subsequently subjecting the reaction mixture to dehydrogenation without recovery of the compound.

Process II
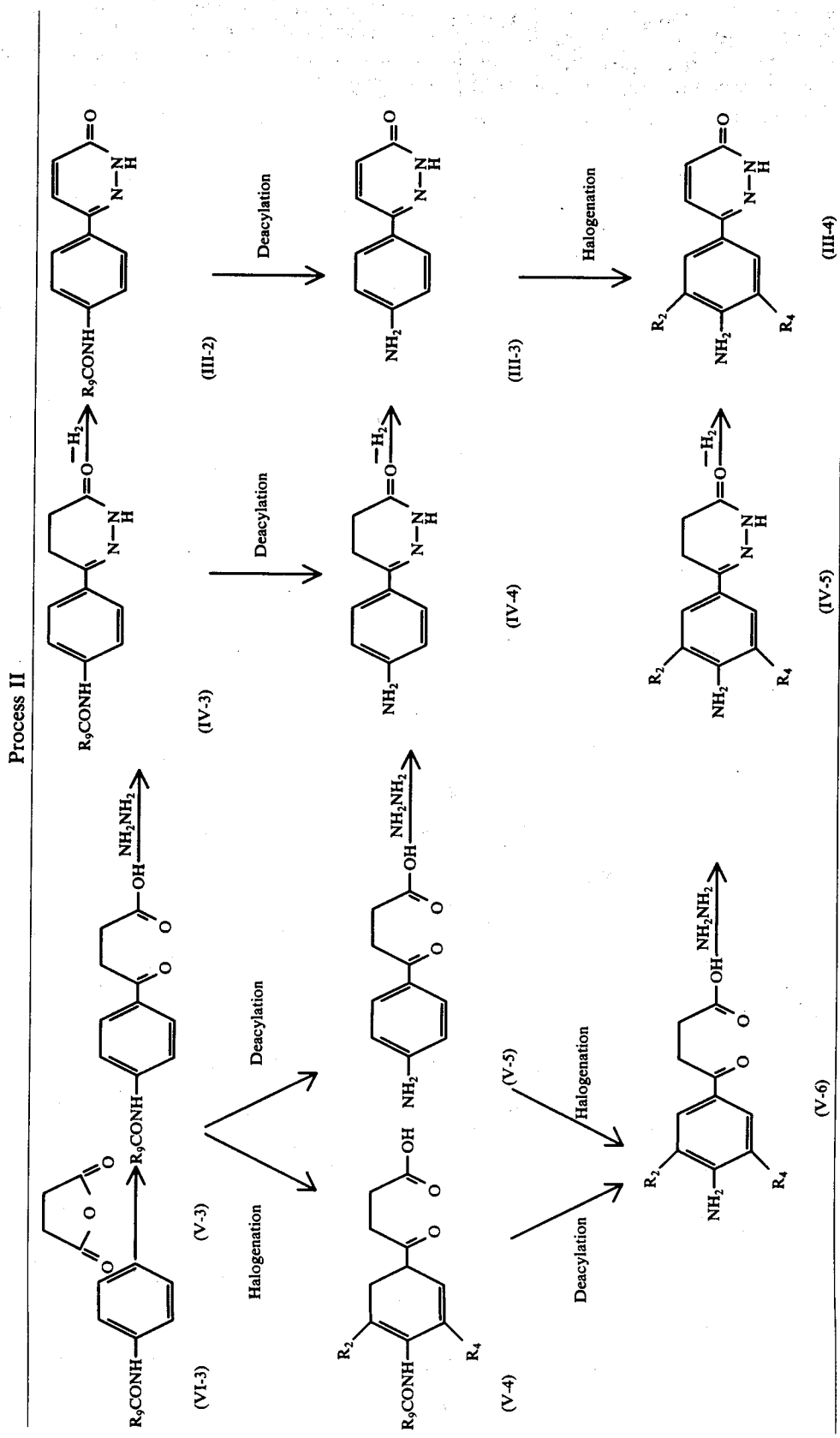
(In the formulae, $R_9$ represents a lower alkyl group such as methyl or ethyl, and $R_2$ and $R_4$ are as defined above.)

A compound of the formula (III-4) having an amino group at the 4-position of the benzene ring, which is one of the compounds of the general formula (I) of the present invention, can be also prepared, as shown in the above schemata, by subjecting a 3-(4-acylaminobenzoyl)propionic acid which is obtained by reaction of a 4-acylaminobenzene (VI-3) with succinic anhydride to halogenation, deacylation, reaction with a hydrazine and dehydrogenation in arbitrary order.

The process for preparing a compound of the formula (V-3) by reacting a compound of the above formula (VI-3) with succinic anhydride may be carried out in the manner as described in the aforementioned (c-1).

The process for preparing a compound of the above formula (V-5), (V-6), (IV-4) or (III-3) by reacting a deacylating agent with a compound of the above formula (V-3), (V-4), (IV-3) or (III-2), respectively, may be carried out, according to a conventional method, in an inert solvent in the presence of an acid or a base. As the inert solvent which may be employed, there is no particular limitation if it does not participate in the present reaction, and the following are preferred: an alcohol such as methanol, ethanol, propanol or butanol; an ether such as dioxane or tetrahydrofuran; a ketone such as acetone or methyl ethyl ketone; and water. As an acid and base which may be employed, there may be mentioned an inorganic acid such as hydrochloric acid, sulfuric acid or orthophosphoric acid; and an inorganic base such as sodium hydroxide, potassium hydroxide, sodium carbonate or potassium carbonate. The reaction is carried out at a temperature ranging from room temperature to around a reflux temperature of the solvent.

The process for preparing a compound of the formula (V-4) by reacting a compound of the above formula (V-3) with a halogenating agent may be carried out in an inert solvent in the presence of a Lewis acid in the manner as described in the aforementioned (c-2).

The process for preparing a compound of the formula (V-6) or (III-4) by reacting a halogenating agent with a compound of the formula (V-5) or (III-3), respectively, can be carried out by mere heating in an inert solvent. As the halogenating agent which may be employed, there may be mentioned chlorine, bromine, iodine, iodine monochloride, N-chlorosuccinimide, N-bromosuccinimide, aqueous sodium hypochlorite solution or hydrochloric acid - aqueous hydrogen peroxide solution. As the solvent which may be employed, there is no particular limitation if it does not participate in the present reaction, and the following may be generally employed: a halogenated hydrocarbon such as tetrachloroethane, dichloroethane, dichloromethane, carbon tetrachloride or chloroform; an organic acid such as acetic acid or propionic acid; or water. The reaction is carried out at a temperature ranging from room temperature to around a reflux temperature of the solvent. The reaction period of time may vary depending upon the reaction temperature, sort of reagent employed, but it is usually about 1 to 24 hours.

The process for preparing a compound of the formula (IV-3), (IV-4) or (IV-5) by reacting a hydrazine with a compound of the formula (V-3), (V-5) or (V-6), respectively, may be carried out in the manner as described in the aforementioned (c-3).

The process for preparing a compound of the formula (III-2), (III-3) or (III-4) by reacting a dehydrogenating agent with a compound of the formula (IV-3), (IV-4) or (IV-5), respectively, may be carried out in the manner as described in the aforementioned (a).

Process III

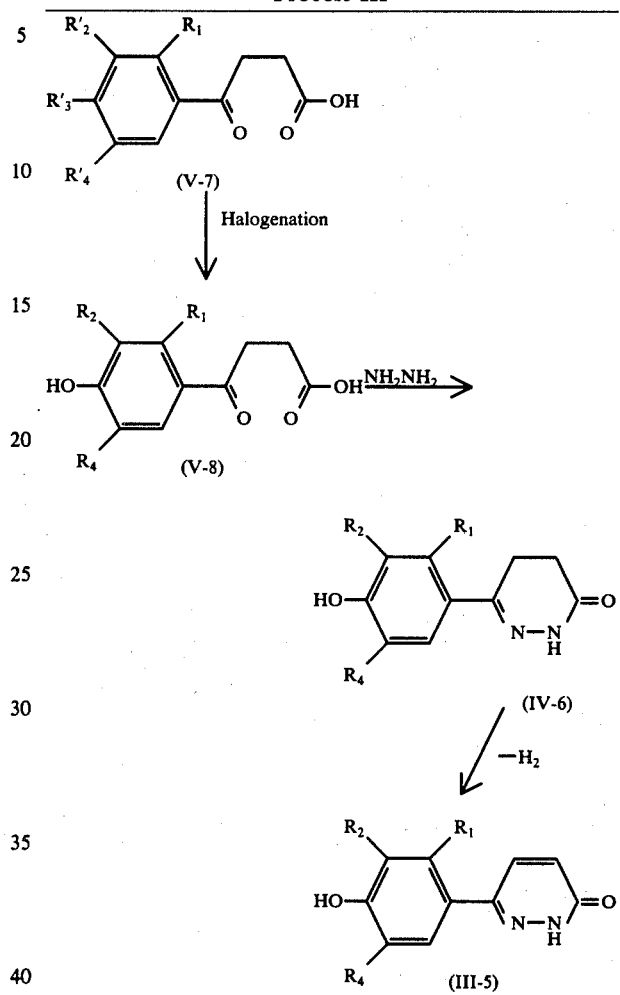

(In the formulae, R'₃ represents a lower alkoxy group such as methoxy, and R₁, R₂, R₄, R'₂ and R'₄ are as defined above.)

Of the compounds having the general formula (I) of the present invention, a compound of the formula (III-5) having a hydroxy group at the 4-position of the benzene ring may be prepared by reaction of a 3-(4-hydroxybenzoyl)-propionic acid (V-8) with a hydrazine and by the following dehydrogenation of the resulting compound. The above-mentioned 3-(4-hydroxybenzoyl)-propionic acid can be obtained from a 3-(4-alkoxybenzoyl)propionic acid (V-7) through halogenation and dealkylation, the latter automatically occuring simultaneously with the former reaction.

The process for preparing a compound of the formula (V-8) by reacting a compound of the formula (V-7) with a halogenating agent whereby halogenation and dealkylation take place may be carried out in an inert solvent in the presence of a Lewis acid according to the method described in the aforementioned (c-2).

The process for preparing a compound of the formula (IV-6) by reacting a compound of the formula (V-8) with a hydrazine may be carried out in the manner as described in the aforementioned (c-3).

The process for preparing a compound of the formula (III-5) by reacting a compound of the formula (IV-6) with a dehydrogenating may be carried out in the manner as described in the aforementioned (a).

Process IV

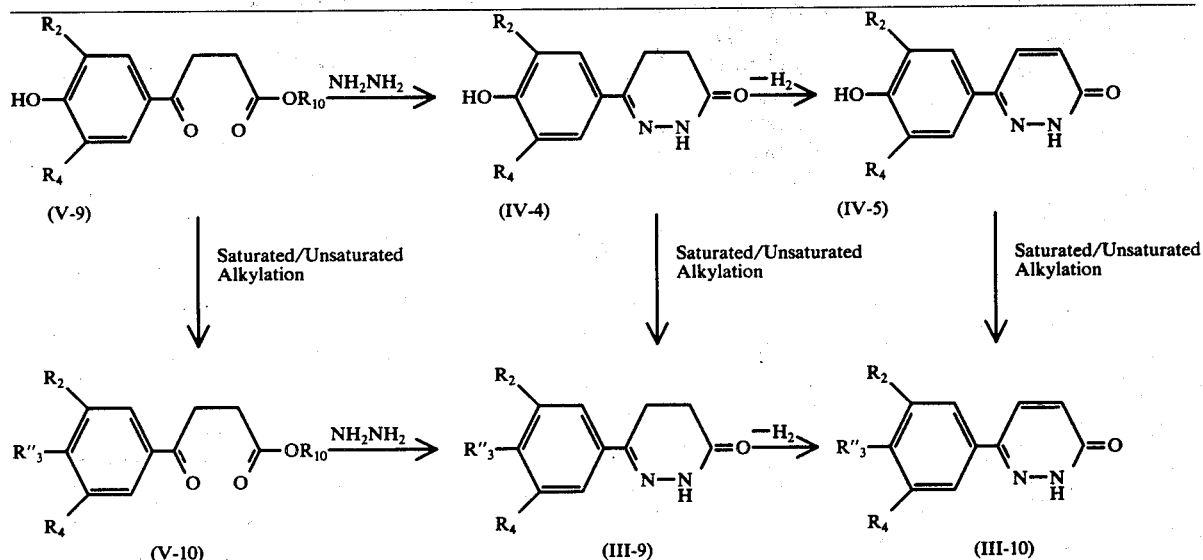

(In the formulae, $R_{10}$ is an alkyl group such as methyl, ethyl or propyl, $R''_3$ is an alkoxy group, an alkenyloxy group or an alkynyloxy group, $R_2$ and $R_4$ are as defined above.)

As shown above, a compound of the formula (III-9) or (III-10), namely a compound having an alkoxy group, an alkenyloxy group or an alkynyloxy group at the 4-position in the phenyl moiety can also be prepared by (A) subjecting a 3-(4-hydroxybenzoyl)propionic acid or an ester thereof (V-9) in optional order to alkylation, alkenylation or alkynylation and a reaction with a hydrazine to form a 6-(4-substitutedphenyl)-4,5-dihydro-3(2H)pyridazinone (III-9) followed by dehydrogenation, (B) reacting the compound (V-9) with a hydrazine to form the compound (IV-4) followed by dehydrogenation to form a 6-(4-hydroxyphenyl)-3(2H)pyridazinone (IV-5) and then subjecting the latter to alkylation, alkenylation or alkynylation, or (C) treating the compound (V-9) with a hydrazine to form the compound (IV-4), which is then alkylated, alkenylated or alkynylated and dehydrogenated as above.

A compound of the formula (V-9) wherein $R_{10}$ is an alkyl group is prepared by conventional esterification of the 3-(4-hydroxybenzoyl)propionic acid produced as described in the Process III. The alkylation of a compound (V-9), (IV-4) or (IV-5) to form a compound (V-10), (III-9) or (III-10) can be effected in an inert solvent, preferably in the presence of a catalyst. As examples of the saturated or unsaturated alkylation agent which may be employed in this reaction, there may be mentioned a dialkyl sulfate such as dimethyl sulfate or diethyl sulfate; a halogenated saturated or unsaturated alkyl such as methyl iodide, ethyl iodide, ethyl bromide, propyl bromide, methyl chloride, allyl bromide, 2-methyl-3-bromo-1-propene or 3-bromo-1-propyne; a trialkyl phosphite such as trimethyl phophite or triethyl phosphite or diazomethane.

In case the saturated or unsaturated alkylating agent is a dialkyl sulfate or a halogenated alkyl, the reaction is preferably effected in the presence of a catalyst. As the catalyst, there may be usually employed, for example, an inorganic base such as sodium hydroxide, potassium hydroxide, sodium carbonate or potassium carbonate; a tertiary amine such as triethylamine, triethylene diamine or N,N-dimethylaniline and the like. As the inert solvent, there is no particular limitation if it does not participate in the reaction and one may use an alcohol such as methanol, ethanol or isopropanol; a ketone such as acetone or methyl ethyl ketone; an ether such as diethyl ether, tetrahydrofuran or dioxane; an aromatic hydrocarbon such as benzene, toluene or xylene; a dialkylformamide such as dimethylformamide or diethylformamide; water and the like.

The process wherein the compound (V-9) or (V-10) is reacted with hydrazine to produce the compound (IV-4) or (III-9) is conducted in the same manner as in the above Process I, step (c-3).

The process wherein the compound (IV-4) or (III-9) is reacted with a dehydrating agent to produce the compound (IV-5) or (III-10) is conducted in the same manner as in the above Process I, step (a).

Process V

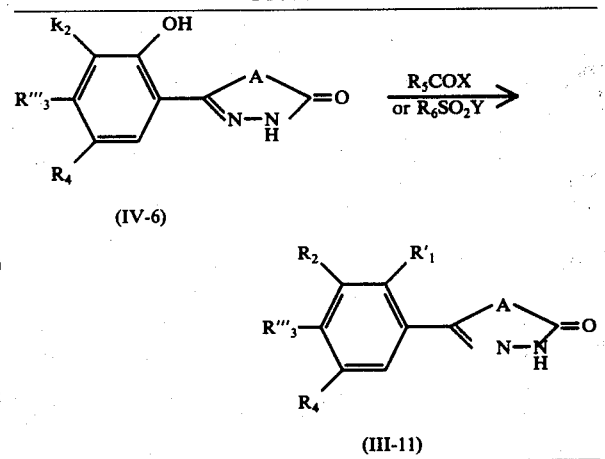

(In the formulae, $R'''_3$ is hydrogen atom, an alkyl group, an alkoxy group, an alkenyloxy group, an alkynyloxy group or a halogen atom, $R'_1$ is the group $-O-CO-R_5$ or $-O-SO_2-R_6$ (wherein $R_5$ and $R_6$ are as defined above), X is a halogen atom or the group $-O-CO-R_5$ (wherein $R_5$ is as defined above), Y is a halogen atom and $R_2$, $R_4$ and A are as defined above.)

Of the compounds of the formula (I) of the present invention, a compound of the formula (IV-6) having the group -O-CO-$R_5$ or -O-SO$_2$-$R_6$ (wherein $R_5$ and $R_6$ are as defined above) at the 2-position of the benzene ring may also be prepared by reacting a 6-(2-hydroxyphenyl)-

3(2H)pyridazinone (IV-6) with a halide or anhydride of a carboxylic acid or with a benzenesulfonic acid halide.

The process wherein the compound (IV-6) is reacted with an acylating agent or a benzenesulfonic acid halide to form the compound (III-11) may be conducted in an inert solvent in the presence or absence of a catalyst. As the acylating agent which may be employed in the reaction may be employed a lower aliphatic acid halide or anhydride such as acetyl chloride, propionyl chloride, butyryl chloride, isovaleryl chloride, hexanyl chloride, acetic anhydride, propionic anhydride or butyric anhydride. As the benzenesulfonic acid halide may be employed benzenesulfonyl chloride, p-toluenesulfonyl chloride, p-chlorobenzenesulfonyl chloride or 2,4-dichlorobenzenesulfonyl chloride.

In case the benzenesulfonic acid halide or the lower aliphatic acid halide as an acylating agent is to be used, the reaction is preferably conducted in the presence of a catalyst. As the catalyst, there may be usually employed, for example, an inorganic base such as sodium hydroxide, potassium hydroxide, sodium carbonate or potassium carbonate; a tertiary amine such as triethylamine, triethylene diamine or N,N-dimethylaniline and the like. As the inert solvent, there is no particular limitation if it does not participate in the reaction and one may use a ketone such as acetone or methyl ethyl ketone; an ether such as diethyl ether, tetrahydrofuran or dioxane; an aromatic hydrocarbon such as benzene, toluene or xylene; a halogenated alkane such as chloroform, dichloromethane or dichloroethane; a dialkylformamide such as dimethylformamide or diethylformamide; an organic acid such as acetic acid, propionic acid or butyric acid and the like. The reaction may be effected at a temperature ranging from room temperature to a reflux temperature of the solvent employed.

Process VI

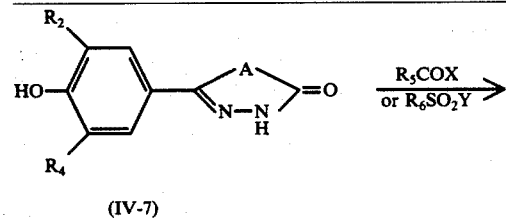

(IV-7)

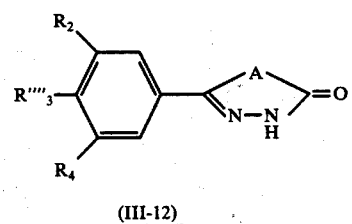

(III-12)

(In the formulae, R''''$_3$ is the group —O—CO—R$_5$ or —CO—R$_5$ or —O—SO$_3$—R$_6$ (wherein R$_5$ and R$_6$ are as defined above),
X is a halogen atom or the group —O—CO—R$_5$ (wherein R$_5$ is as defined above), Y is a halogen atom and R$_2$, R$_4$ and A are as defined above.)

Of the compounds of the formula (I) of the present invention, a compound of the formula (III-12) having the group -O-CO-R$_5$ or -O-SO$_2$-R$_6$ (wherein R$_5$ and R$_6$ are as defined above) at the 4-position of the benzene ring is prepared by reacting a 6-(4-hydroxyphenyl)-3(2H)pyridazinone (IV-7) with a carboxylic acid halide or anhydride or with a benzenesulfonic acid halide.

The process wherein the compound (IV-7) is reacted with the acylating agent or the benzenesulfonic acid halide to form a compound (III-12) may be effected in the same manner as in the above Process V.

PROCESS VII

An acid addition salt of a compound having the formula (I) wherein A is -CH=CH- with a mineral acid is easily formed by intimately contacting the compound (I) with the mineral acid in an appropriate solvent. As the solvent which may be employed, there is no critical limitation. For example, water; an alcohol such as methanol or ethanol; an ether such as tetrahydrofuran or dioxane; an aromatic hydrocarbon such as benzene; a halogenated hydrocarbon such as dichloromethane or chloroform; a ketone such as acetone or a mixture thereof with water may be preferably employed. Generally, a salt with a mineral acid is formed at a pH range of not more than about 3 in a solution.

A salt of a compound having the formula (I) wherein A is -CH=CH- with a metal is formed by treating a solution of the compound of the formula (I) with a cation in the presence of a solvent. As the solvent for the formation of the above-mentioned salt, there is no particular limitation. For example, water; an alcohol such as methanol or ethanol; an ether such as tetrahydrofuran or dioxane; an aromatic hydrocarbon such as benzene; a halogenated aliphatic hydrocarbon such as dichloromethane or chloroform or a mixture thereof with water may be preferably employed. Various salts may be formed wherein a coordination ratio of a compound having the formula (I) to the cation may vary as 1:1, 1:2, or 1:3, depending upon valency of the cation and the solvent applied.

An adduct of a compound having the formula (I) wherein A- is -CH=CH- with an alkyl isocyanate is formed by reacting the compound (I) with the alkyl isocyanate in the presence or absence of a solvent. There is no particular limitation on the sort of solvents if they do not participate in the reaction and one may usually employ, for example, toluene, xylene, dimethylformamide, dimethylsulfoxide, dioxane, tetrahydrofuran, ethylene glycol diethyl ether or acetonitrile. The reaction temperature is not critical, but it is usually a temperature under cooling to a reflux temperature of the solvent employed, advantageously room temperature.

The compounds of the above formula (I) and salts thereof are employed as agricultural fungicides and show a preventive and curative effect against plant diseases without any damage upon host plants.

More specifically, they can particularly effectively control sheath blight of rice plants which is a serious disease in rice plants by using a spray or a surface spray.

Also, they are particularly effective in controlling damping-off of various crops such as beets, cotton plants, gourd family which is caused by pathogenic fungi Rhizoctonia and effective in controlling infectious soil-borne diseases, e.g., southern blight of egg plants and gourd family plants, black scurf or potatoes and the like by use as a soil fungicide or a seed disinfectant.

In a practical dose are not found any phytotoxicities in crops such as rice plants, tomatoes, potatoes, cotton plants, egg plants, cucumbers, kidney beans and so on.

Additionally, the compounds of the above formula (I) or salts thereof are effectively usable as fungicides in an orchard, a non-crop land, a forest and so on.

The compounds in this invention may be formulated for use to a preparation commonly employed as an agricultural fungicide, for example, powdery dusts, coarse dusts, fine granules, wettable powders, emulsifiable concentrates, aqueous liquids, water soluble powders, oil suspensions and so on, with admixture of a carrier and, if required, other auxiliary agents. The carrier as used herein means a synthetic or natural and inorganic or organic substance that is mixed with an active compound and can assist an active compound in its arrival to the portion to be treated and make it easy to store, transport or handle.

As suitable solid carriers may be mentioned inorganic substances such as clays, which may be represented by Kaolinite, Montmorillonite or Attapulgite, talc, mica, pyrophyllite, pumice, vermiculite, gypsum, calcium carbonate, dolomite, diatomaceous earth, magnesium carbonate, apatite, zeolite, silicic anhydride, synthetic calcium silicate and the like, vegetable organic substances such as soybean meal, tobacco powder, walnut powder, wheat flour, wood meal, starch, crystalline cellulose and the like, synthetic or natural high polymer compounds such as cumarone resin, petroleum resin, alkyd resin, polyvinyl chloride, polyalkylene glycol, ketone resin, ester gum, copal gum, dammar gum, and the like, waxes such as carnauba wax, beeswax and the like or urea.

As suitable liquid media or carriers may be mentioned paraffin or naphthene hydrocarbons such as kerosine, mineral oil, spindle oil, white oil and the like, aromatic hydrocarbons such as benzene, toluene, xylene, ethylbenzene, cumene, methylnaphthalene and the like, chlorinated hydrocarbons such as carbon tetra-chloride, chloroform, trichloroethylene, monochlorobenzene, o-chlorotoluene and the like, ethers such as dioxane, tetrahydrofuran and the like, ketones such as acetone, methyl ethyl ketone, diisobutylketone, cyclohexanone, acetophenone, isophorone and the like, esters such as ethyl acetate, amyl acetate, ethylene glycol acetate, diethylene glycol acetate, dibutyl maleate, diethyl succinate and the like, alcohols such as methanol, n-hexanol, ethylene glycol, diethylene glycol, cyclohexanol, benzyl alcohol and the like, ether alcohols such as ethylene glycol ethyl ether, ethylene glycol phenyl ether, diethylene glycol ethyl ether, diethylene glycol butyl ether and the like, polar solvents such as dimethylformamide, dimethylsulfoxide and the like or water.

As the surface active agents used for emulsifying, dispersing, wetting, spreading, binding, controlling disintegration, stabilizing active ingredient, improving fruidity, rust proofing and so on may be utilized any of non-ionic, anionic, cationic and amphoteric ones, but non-ionic and/or anionic agents are usually employed. As suitable non-ionic surface active agents may be mentioned, for example, polymerization adducts of ethylene oxide to higher alcohols such as lauryl alcohol, stearyl alcohol, oleyl alcohol and the like, polymerization adducts of ethylene oxide to alkyl phenols such as isooctyl phenol, nonyl phenol and the like, polymerization adducts of ethylene oxide to alkyl naphthols such as butyl naphthol, octyl naphthol and the like, polymerization adducts of ethylene oxide to higher fatty acids such as palmitic acid, stearic acid, oleic acid and the like, polymerization adducts of ethylene oxide to mono- or dialkyl phosphoric acids such as stearyl phosphoric acid, dilauryl phosphoric acid and the like, polymerization adducts of ethylene oxide to amines such as dodecyl amine, stearic acid amide and the like, polymerization adducts of ethylene oxide to higher fatty acid esters of polyhydric alcohols such as sorbitan and said fatty acid esters, polymerization adducts of ethylene oxide to propylene oxide and so on. As suitable anionic surface active agents may be mentioned, for example, alkyl sulfate salts such as sodium lauryl sulfate, oleyl sulfate amine salt and the like, alkyl sulfonate salts such as sodium dioctyl sulfosuccinate, sodium 2-ethylhexene sulfonate and the like, aryl sulfonate salts such as sodium isopropylnaphthalene sulfonate, sodium methylenebisnapthalene sulfonate, sodium ligninsulfonate, sodium dodecylbenzene sulfonate and the like.

Moreover, the agricultural fungicidal compositions of this invention may be used in combination with high molecular compounds or other auxiliary agents such as casein, gelatin, albumin, glue, sodium alginate, carboxymethyl cellulose, methyl cellulose, hydroxyethyl cellulose, polyvinyl alcohol and the like for improving properties and increasing biological effects thereof.

The above-mentioned carriers and various auxiliary agents may be optionally utilized alone or in combination therewith for desired purposes, with consideration for the type of a preparation, application and other factors.

Dusts usually contain, for example, 1 to 25 parts by weight of the active compound and the remainder is a solid carrier.

Wettable powders usually contain, for example, 25 – 90 parts by weight of the active compound and the remainder is a solid carrier and a dispersing and wetting agent, if required, together with a protective colloidal agent, a thixotropic agent, an anti-foaming agent and the like.

Granules usually contain 1 – 35 parts by weight of the active compound and a major portion of the remainder is a solid carrier. The active compound is homogeneously admixed with the solid carrier or adhered or adsorbed on the carrier surface and the size of a granule is about 0.2 – 1.5 mm.

Emulsifiable concentrations usually contain, for example, 5 – 50 parts by weight of the active compound and about 5 – 20 parts by weight of an emulsifying agent, the remainder being a liquid carrier, if required, together with a corrosive inhibitor.

The fungicidal compositions of this invention which are formulated into various types of preparations as above, may be applied in a paddy or upland field at 1 – 5000 g, preferably 10 – 1000 g of the active ingredient per 10 acres for pre- or post-emergency foliage spraying or soil drenching or spraying onto water to control diseases effectively.

Further, the fungicidal compositions of this invention, when employed for seed disinfection or coating, may effectively control soil-borne or seed infectious diseases by coating seeds at 0.1 – 2%, preferably 0.2 – 0.5% of the active ingredient per weight of the seed.

The fungicidal compositions of this invention may be preferably combined with other fungicides for broader fungicidal spectra and, in some cases, a synergistic effect is expectable.

As examples of such other fungicides may be, for instance, carbamate type fungicides such as 3,3'-ethylene-bis(tetrahydro-4,6-dimethyl-2H-1,3,5-thiadiazine-2-thione; zinc or manganese ethylenebisdithiocarbamate; bis(dimethyldithiocarbamoyl)disulfide; zinc propylenebisdithiocarbamate; bis(dimethyldithiocarbamoyl)ethylenediamine; nickel dimethyldithiocarbamate; methyl 1-(butylcarbamoyl)-2-benzimidazolcarbamate; 1,2-bis(3-methoxycarbonyl-2-thioureido)benzene; 1-isopropylcarbamoyl-3-(3,5-dichlorophenyl)hydantoin; potassium N-hydroxymethyl-N-methyldithiocarbamate; 5-methyl-10-butoxycarbonylamino-10,11-dehydrodibenzo(b,f)azepine and the like; pyridine type fungicides such as zinc bis(1-hydroxy-2(1H)pyridinethionate); sodium 2-pyridinethiol-1-oxide and the like, phosphorous type fungicides such as O,O-diisopropyl-S-benzylphosphorothioate; O-ethyl-S,S-diphenyldithiophosphate and the like, phthalimide type fungicides such as N-(2,6-diethylphenyl)phthalimide; N-(2,6-diethylphenyl)-4-methylphthalimide and the like, dicarboximide type fungicides such as N-trichloromethylthio-4-cyclohexane-1,2-dicarboximide; N-tetrachloroethylthio-4-cyclohexene-1,2-dicarboximide and the like, oxazine type fungicides such as 5,6-dihydro-2-methyl-1,4-oxazine-3-carboxanilide-4,4-dioxide; 5,6-dihydro-2-methyl-1,4-oxazine-3-carboxanilide and the like, naphthoquinone type fungicides such as 2,3-dichloro-1,4-naphthoquinone, 2-oxy-3-chloro-1,4-naphthoquinone copper sulfate and the like, other fungicides such as pentachloronitrobenzene; 1,4-dichloro-2,5-dimethoxybenzene; 5-methyl s-triazole(3,4-b)-benzthiazole; 2-(thiocyanomethylthio)benzthiazole; 3-hydroxy-5-methylisoxazole; N-2,3-dichlorophenyltetrachlorophthalamidic acid; 5-ethoxy-3-trichloromethyl-1,2,4-thiadiazole; 2,4,6-trichloro-6-(o-chloroanilino)-1,3,5-triazine; 2,3-dicyano-1,4-dithioanthraquinone; copper 8-quinolate; polyoxin; validamycin; cycloheximide; iron methanearsonate; diisopropyl-1,3-dithioran-2-ylidene malonate; 3-allyloxy-1,2-benzoisothiazole 1,1-dioxide, Kasugamycin; Blasticidin S; 4,5,6,7-tetrachlorophthalide and the like, but they are not critical.

The fungicidal compositions of this invention may also be applied in admixture with plant growth regulators, herbicides or insecticides as illustratively given below.

Isourea type plant growth regulators such as N-methoxycarbonyl-N'-4-methylphenylcarbamoylethyl isourea, 1-(4-chlorophenylcarbamoyl)-3-ethoxycarbonyl-2-methyl isourea and the like, plant growth regulators such as sodium naphthyl acetate; 1,2-dihydropyridazine-3,6-dione; gibberellins and the like, triazine type herbicides such as 2-methylthio-4,6-bisethylamino-1,3,5-triazine, 2-chloro-4,6-bisethylamino-1,3,5-triazine; 2-methoxy-4-ethylamino-6-isopropylamino-1,3,5-triazine; 2-chloro-4-ethylamino-6-isopropylamino-s-triazine; 2-methylthio-4,6-bis(isopropylamino)-s-triazine; 2-methylthio-4-ethylamino-6-isopropylamino-s-triazine and the like, phenoxy type herbicides such as 2,4-dichlorophenoxyacetic acid and its methyl, ethyl or butyl ester; 2-chloro-4-methylphenoxyacetic acid; 4-chloro-2-methylphenoxyacetic acid, ethyl 2-methyl-4-chlorophenoxybutyrate and the like, diphenyl ether type herbicides such as 2,4,6-trichlorophenyl-4'-nitrophenyl ether; 2,4-dichlorophenyl-4'-nitrophenyl ether; 3,5-dimethylphenyl-4'-nitrophenyl ether and the like, urea type herbicides such as 3-(3,4-dichlorophenyl)-1-methoxy-1-methylurea; 3-(3,4-dichlorophenyl)-1,1-dimethylurea; 3-(4-chlorophenyl)-1,1-dimethylurea and the like, carbamate type herbicides such as 3-methoxycarbonylaminophenyl-N-(3-methylphenyl)-carbamate; isopropyl N-(3-chlorophenyl)carbamate; methyl N-(3,4-dichlorophenyl)carbamate and the like, uracil type herbicides such as 5-bromo-3-sec-butyl-6-methyluracil; 1-cyclohexyl-3,5-propyleneuracil and the like, thiocarbamate type herbicides such as S-(4-chlorobenzyl)-N,N-diethylthiolcarbamate; S-ethyl-N-cyclohexyl-N-ethylthiolcarbamate; S-ethyl-hexahydro-1H-azepine-1-carbothioate; S-ethyl-N,N-di-n-propylthiocarbamate and the like, pyridinium salt type herbicides such as 1,1'-dimethyl-4,4'-bispyridinum dichloride and the like, phosphorus type herbicides such as N-(phosphonomethyl)glycine and the like, aniline type herbicides such as α,α,α-trifluoro-2,6-dinitro-N,N-dipropyl-p-toluidine; 4-(methylsulfonyl)-2,6-dinitro-N,N-dipropylaniline and the like, acid anilide type herbicides such as 2-chloro-2',6'-diethyl-N-(butoxymethyl)acetanilide; 2-chloro-2',6'-diethyl-N-(methoxymethyl)acetanilide; 3,4-dichloropropionanilide and the like, pyrazole type herbicides such as 1,3-dimethyl-4-(2,4-dichlorobenzoyl)-5-hydroxypyrazole; 1,3-dimethyl-4-(2,4-dichlorobenzoyl)-5-(p-toluenesulfonyloxy)pyrazole and the like, 5-tert-butyl-3-(2,4-dichloro-5-isopropoxyphenyl)-1,3,4-oxadiazolin-2-one; 2-(N-isopropyl-N-(4-chlorophenyl)carbamoyl)-4-chloro-5-methyl-4-isoxazolin-3-one; 3-isopropylbenzo-2-thia-1,3-diazinon-(4)-2,2-dioxide; 3-(2-methylphenoxy)pyridazine and the like, phosphorus type insecticides such as O,O-diethyl O-(2-isopropyl-4-methyl-6-pyrimidinyl)phosphorothioate; O,O-diethyl S-2-[(ethylthio)ethyl]phosphorodithioate; O,O-dimethyl O-(3-methyl-4-nitrophenyl)thiophosphate; O,O-dimethyl S-(N-methylcarbamoylmethyl)phosphorodithioate; O,O-dimethyl S-(N-methyl-N-formylcarbamoylmethyl)-phosphorodithioate; O,O-dimethyl S-2-(ethylthio)ethylphosphorodithioate; O,O-diethyl S-2-[(ethylthio)ethyl]phosphorodithioate; O,O-dimethyl-1-hydroxy-2,2,2-trichloroethylphosphonate; O,O-diethyl-O-(5-phenyl-3-isoxazolyl)phosphorothioate; methyl(4-bromo-2,5-dichlorophenyl)phenylphosphonothioate; O,O-dimethyl-O-(3-methyl-4-methylmercaptophenyl)-thiophosphate; O-ethyl-O-p-cyanophenyl phenylphosphonothioate; O,O-diethyl S-(1,2-dicarboethoxyethyl)-phosphorodithioate; 2-chloro-1-(2,4,5-trichlorophenyl)-vinyldimethyl phosphate; 2-chloro-1-(2,4-dichlorophenyl)-vinyldimethyl phosphate; O,O-dimethyl O-p-cyanophenyl phosphorothioate; 2,2-dichlorovinyl dimethyl phosphate; O,O-diethyl O-2,4-dichlorophenyl phosphorothioate; ethyl mercaptophenylacetate O,O-dimethyl phosphorodithioate; S-[(6-chloro-2-oxo-3-benzooxazolinyl)-methyl]O,O-diethylphosphorodithioate; 4-mercaptothiophenyl dipropylphosphate; 2-chloro-1-(2,4-dichlorophenyl)vinyl diethylphosphate; O,O-diethyl-O-(3-oxo-2-phenyl-2H-pyridazin-6-yl)phosphorothioate; O,O-dimethyl S-(1-methyl-2-ethylsulfinyl)-ethyl phosphorothiolate; O,O-dimethyl S-phthalimidomethyl phosphorodithioate; dimethylmethylcarbamoylethylthioethyl thiophosphorothiolate; O,O-diethyl S-(N-ethoxycarbonyl-N-methylcarbamoylmethyl)phosphorodithioate; O,O-dimethyl-S-[2-methoxy-1,3,4-thiadiazol-5(4H)-onyl-(4)-methyl] dithiophosphate; 2-methoxy-4H-1,3,2-benzodioxaphosphorin 2-sulfide; O,O-diethyl-O-(3,5,6-trichloro-2-pyridyl)phosphorothioate; O-ethyl-O-2,4-dichlorophenyl thionobenzene phosphonate; S-[4,6-diamino-S-triazin-2-yl-methyl]-O,O-dimethyl phosphorodithioate; O-ethyl O-p-nitrophenylphenylphosphorothioate; O,S-dimethyl-N-acetyl phosphoroamidothioate; 2-diethylamino-6-methyl-pyrimidin-4-yl-diethylphosphorothioate; O,O-diethyl O-p-(methylsulfinyl)-phenyl phosphorothioate; O-ethyl-S-propyl O-2,4-dichlorophenylphosphorodithioate; cis-3-(dimethoxyphosphinoxy)-N-methyl-cis-crotonamide and the like, carbamate type insecticides such as 1-naphthyl N-methylcarbamate; S-methyl-N-[methylcarbamoyloxy]thioacetoimidate; m-tolyl methylcarbamate; 3,4-xylyl methylcarbamate; 3,5-xylyl methylcarbamate; 2-sec-butylphenyl-N-methylcarbamate; 2,3-dihydro-2,2-dimethyl-7-benzofuranylmethylcarbamate; 2-isopropoxyphenyl-N-methylcarbamate; 1,3-bis(carbamoylthio)-2-(N,N-dimethylamino)propane hydrochloride; 2-diethylamino-6-methylpyrimidin-4-yl dimethyl carbamate and the like, other insecticides such as N,N-dimethyl-N'-(2-methyl-4-chlorophenyl) formamidine hydrochloride, nicotine sulfate, silbemycin, 6-methyl-2,3-quinoxalinedithiocyclic S,S-dithiocarbonate, 2,4-dinitro-6-sec-butylphenyl dimethylacrylate; 1,1-bis(p-chlorophenyl)-2,2,2-trichloroethanol; 2-(p-tert-butylphenoxy)isopropyl-2'-chloroethylsulfite; azoxybenzene; di-(p-chlorophenyl)-cyclopropyl carbinol; di[tri(2,2-dimethyl-2-phenylethyl)-tin]oxide; 1-(4-chlorophenyl)-3(2,6-difluorobenzoyl)urea; S-tricyclohexyltin O,O-diisopropyl phosphorodithioate and the like or fertilizers and so on.

A agricultural fungicidal composition of this invention can be used with a controlling agent against rice blast, Helminthosporium leaf spot, bacterial leaf blight, rice stem borer, planthopper and/or leafhopper to make labor-saving effectively. The agricultural chemicals, which may be used with the present fungicidal composition, are as mentioned hereinabove. A combination ratio of these agents may vary depending upon diseases or insects to be controlled and preparation forms to be used. These agents are prepared and applied with an effective amount of active ingredients required for controlling. In particular, dusts are preferable for controlling rice plant diseases and soil treatment.

The preparation of a compound having the above formula (I) or (II) and a fungicidal composition containing a compound having the above formula (I) will be more fully illustrated by way of the following examples.

EXAMPLES OF SYNTHESIS

EXAMPLE 1

6-(3,5-dichloro-4-methylphenyl)-3(2H)pyridazinone (1) To a suspension of 19.22 g. of 4-(4-methylphenyl)-4-oxobutyric acid in one liter of dichloroethane was carefully added 400 g. of aluminum chloride while stirring at a temperature of not higher than 10° C. Then, the reaction vessel was cooled to 0° C. and about 175.5 g. of chlorine gas was introduced therein over 13 hours. After leaving overnight, the reaction mixture was poured into a mixture of 1.8 Kg. of ice and 300 ml. of conc. hydrochloric acid with vigorous stirring. After leaving for a while, the so separated upper layer was removed by decantation and 800 ml. of n-hexane was added to the lower layer to separate a crystalline substance. The substance was recovered by filtration, washed with water until the washing became approximately neutral, dried and then recrystallized from 1.8 l. of toluene to give 156.2 g. of crude crystals. The so obtained crystals were recrystallized from 2 l. of acetonitrile to give 135.3 g. of 4-(3,5-dichloro-4-methylphenyl)-4-oxobutyric acid as colorless needles of m.p. 185°-187° C.

(2) In 120 ml. of ethanol was dissolved 15.6 g. of 4-(3,5-dichloro-4-methylphenyl)-4-oxobutyric acid by heating to about 50° C. and then 3.28 g. of hydrazine hydrate was added dropwise with stirring to the resulting solution. After completion of the dropwise addition, the mixture was heated under reflux for about 1 hour. After cooling, the so separated crystalline substance was recovered by filtration, washed with ethanol and dried to afford 13.4 g. of 6-(3,5-dichloro-4-methylphenyl)-4,5-dihydro-3(2H)pyridazinone as colorless needles of m.p. 204° - 205° C.

(3) To a suspension of 9.5 g. of 6-(3,5-dichloro-4-methylphenyl)-4,5-dihydro-3(2H)pyridazinone in acetic acid at 70° C. was added dropwise 7.2 g. of bromine with stirring. After completion of the dropwise addition, the resulting mixture was heated under reflux for 1 hour. After leaving overnight, the so separated crystalline substance was recovered by filtration, washed with cooled ethyl acetate and dried to give the hydrobromide of the desired product having m.p. 258° - 262° C. (dec.) This product was suspended in 50 ml. of water and neutralized with conc. aqueous ammonia. The resulting solid substance was recovered by filtration, washed with water and dried to give 9.4 g. of the desired product as colorless needles of m.p. 254° - 258° C.

Following the procedures as described in the above-mentioned Example 1-(1), there were produced the following compounds.

4-(3-chloro-4-methylphenyl)-4-oxobutyric acid, m.p. 151° - 153° C.
4-(3-bromo-4-methylphenyl)-4-oxobutyric acid, m.p. 165° - 171° C.
4-(3-chloro-4-isopropylphenyl)-4-oxobutyric acid, m.p. 117° - 118° C.
4-(3,5-dibromo-4-methylphenyl)-4-oxobutyric acid, m.p. 188° - 191° C.
4-(3,5-dichloro-4-ethylphenyl)-4-oxobutyric acid, m.p. 137° - 138° C.
4-(3,5-dichloro-4-n-propylphenyl)-4-oxobutyric acid, m.p. 133° - 134° C.
4-(3,5-dichloro-2-hydroxy-4-methylphenyl)-4-oxobutyric acid, m.p. 185° - 187° C.
4-(3-chloro-4-ethylphenyl)-4-oxobutyric acid, m.p. 160° - 161° C.
4-(3-bromophenyl)-4-oxobutyric acid, m.p. 114° - 119° C.
4-(3-chlorophenyl)-4-oxobutyric acid, m.p. 107° - 109° C.
4-(3,5-dichloro-4-n-butylphenyl)-4-oxobutyric acid, m.p. 120° - 122° C.
4-(3-chloro-4-fluorophenyl)-4-oxobutyric acid, m.p. 98° - 101° C.
4-(3-bromo-4-chlorophenyl)-4-oxobutyric acid, m.p. 160° - 163° C.
4-(3-bromo-4-fluorophenyl)-4-oxobutric acid, m.p. 121° - 124° C.
4-(3,4,5-trichlorophenyl)-4-oxobutyric acid, m.p. 159° - 163° C.
4-(3-chloro-4-bromophenyl)-4-oxobutyric acid, m.p. 175° - 178° C.

Following the procedures as described in the above-mentioned Example 1-(2), there were produced the following compounds.

6-(3,4-dichlorophenyl)-4,5-dihydro-3(2H)pyridazinone, m.p. 176° - 179° C.
6-(3-chloro-4-methylphenyl)-4,5-dihydro-3(2H)-pyridazinone, m.p. 160° - 162° C.
6-(3-bromo-4-methylphenyl)-4,5-dihydro-3(2H)-pyridazinone, m.p. 150° - 153° C.
6-(3-chloro-4-isopropylphenyl)-4,5-dihydro-3(2H)-pyridazinone, m.p. 153° - 157° C.
6-(3,5-dibromo-4-methylphenyl)-4,5-dihydro-3(2H)-pyridazinone, m.p. 196° - 202° C.
6-(3,5-dichloro-4-ethylphenyl)-4,5-dihydro-3(2H)-pyridazinone, m.p. 164° - 166° C.
6-(3,5-dichloro-4-n-propylphenyl)-4,5-dihydro-3(2H)pyridazinone, m.p. 205° - 207° C.

6-(3,5-dichloro-2-hydroxy-4-methylphenyl)-4,5-dihydro-3(2H)pyridazinone, m.p. above 300° C.
6-(3-chloro-4-ethylphenyl)-4,5-dihydro-3(2H)-pyridazinone, m.p. 142° – 144° C.
6-(3-bromophenyl)-4,5-dihydro-3(2H)pyridazinone, m.p. 141° – 145° C.
6-(3,5-dichloro-4-n-butylphenyl)-4,5-dihydro-3(2H)pyridazinone, m.p. 174° – 177° C.
6-(3-chloro-4-fluorophenyl)-4,5-dihydro-3(2H)-pyridazinone, m.p. 155° C.
6-(3,5-dichloro-4-isopropylphenyl)-4,5-dihydro-3(2H)pyridazinone, m.p. 202° – 205° C.
6-(3,4-dibromophenyl)-4,5-dihydro-3(2H)pyridazinone, m.p. 181° – 183° C.
6-(3-bromo-4-chlorophenyl)-4,5-dihydro-3(2H)-pyridazinone, m.p. 171° – 173° C.
6-(3-bromo-4-fluorophenyl)-4,5-dihydro-3(2H)-pyridazinone, m.p. 145° – 147° C.
6-(3-chloro-4-bromophenyl)-4,5-dihydro-3(2H)-pyridazinone, m.p. 170° – 172° C.
6-(3,4,5-trichlorophenyl)-4,5-dihydro-3(2H)pyridazinone, m.p. 195° – 199° C.
6-(3,5-dichloro-2-hydroxyphenyl)-4,5-dihydro-3(2H)pyridazinone, m.p. 271° – 273° C.

Following the procedures as described in the above-entioned Example 1 – 3, there were produced the llowing compounds.

6-(3,4-dichlorophenyl)-3(2H)pyridazinone, m.p. 258° – 262° C.
6-(3-chloro-4-methylphenyl)-3(2H)pyridazinone, m.p. 275° – 280° C.
6-(3-bromo-4-methylphenyl)-3(2H)pyridazinone, m.p. 284° – 286° C.
6-(3-chloro-4-isopropylphenyl)-3(2H)pyridazinone, m.p. 200° – 204° C.
6-(3,5-dibromo-4-methylphenyl)-3(2H)pyridazinone, m.p. 242° – 246° C.
6-(3,5-dichloro-4-ethylphenyl)-3(2)pyridazinone, m.p. 254° C.
6-(3,5-dichloro-4-n-propylphenyl)-3(2H)pyridazinone, m.p. 261° C.
6-(3,5-dichloro-2-hydroxy-4-methylphenyl)-3(2H)-pyridazinone, m.p. above 300° C.
6-(3-chloro-4-ethylphenyl)-3(2H)pyridazinone, m.p. 195° – 197° C.
6-(3-bromophenyl)-3(2H)pyridazinone, m.p. 202° – 204° C.
6-(3-chlorophenyl)-3(2H)pyridazinone, m.p. 227° C.
6-(3-chloro-4-methoxyphenyl)-3(2H)pyridazinone, m.p. 287° – 288° C.
6-(3,4-dichlorophenyl)-3(2H)pyridazinone.hydrobromide, m.p. 262° – 266° C. (dec.)
6-(3-bromo-4-methylphenyl)-3(2H)pyridazinone.hydrobromide, m.p. 273° – 278° C. (dec.)
6-(3-chlorophenyl)-3(2H)pyridazinone.hydrobromide, m.p. 227° C. (dec.)
6-(3-bromophenyl)-3(2H)pyridazinone.hydrobromide, m.p. 225° – 229° C. (dec.)
6-(3,4-dibromophenyl)-3(2H)pyridazinone, m.p. 299° – 303° C.
6-(3-chloro-4-fluorophenyl)-3(2H)pyridazinone, m.p. 237° – 239° C.
6-(3-bromo-4-chlorophenyl)-3(2H)pyridazinone, m.p. 289° – 293° C.
6-(3-bromo-4-fluorophenyl)-3(2H)pyridazinone, m.p. 251° – 253° C.
6-(3-chloro-4-bromophenyl)-3(2H)pyridazinone, m.p. 273° – 276° C.
6-(3,5-dichloro-4-isopropylphenyl)-3(2H)pyridazinone, m.p. 248° – 251° C.
6-(3,4,5-trichlorophenyl)-3(2H)pyridazinone, m.p. 243° – 246° C.
6-(3,5-dichloro-4-n-butylphenyl)-3(2H)pyridazinone, m.p. 240° – 241° C.
6-(3,5-dichloro-2-hydroxyphenyl)-3(2H)pyridazinone, m.p. above 300° C.

EXAMPLE 2

6-(3,5-dibromo-2-hydroxy-4-methylphenyl)-3(2H)pyridazinone

1 A mixture of 2.08 g. of 4-(2-hydroxy-4-methylphenyl)-4-oxobutyric acid and 0.75 g. hydrazine hydrate in 20 ml. of methanol was heated under reflux for about 1 hour. After cooling, the so separated crystalline substance was recovered by filtration and washed with methanol to give 1.65 g. of 6-(2-hydroxy-4-methylphenyl)-4,5-dihydro-3(2H)pyridazinone as pale yellow needles of m.p. 210° – 211° C. (Yield 81%).

2 A mixture of 1.0 g. of 6-(2-hydroxy-4-methylphenyl)-4,5-dihydro-3(2H)pyridazinone and 3.0 g. of bromine in 10 ml. of acetic acid was heated under reflux for about 30 minutes. After cooling, 30 ml. of water was added to the reaction mixture and the crystalline substance thus separated was recovered by filtration, washed with water and then with methanol and dried to give 1.65 g. of the desired product as white crystals of m.p. above 280° C. (Yield 92%).

Following the procedures as described in the above-mentioned Example 2 – 1, there were produced the following compounds.

6-(4-chloro-2-hydroxyphenyl)-4,5-dihydro-3(2H)-pyridazinone, m.p. 225° – 230° C.
6-(5-chloro-2-hydroxy-4-methylphenyl)-4,5-dihydro-3(2H)pyridazinone, m.p. above 300° C.
6-(5-chloro-2-hydroxyphenyl)-4,5-dihydro-3(2H)-pyridazinone, m.p. 255° – 257° C.

Following the procedures as described in the above-mentioned Example 2 – 2, there were produced the following compounds.

6-(4-chloro-3,5-dibromo-2-hydroxyphenyl)-3(2H)-pyridazinone, m.p. above 280° C.
6-(3-bromo-5-chloro-2-hydroxy-4-methylphenyl)-3(2H)pyridazinone, m.p. above 300° C.
6-(3-bromo-5-chloro-2-hydroxyphenyl)-3(2H)pyridazinone, m.p. above 280° C.

EXAMPLE 3

6-(5chloro2-hydroxy-4-methylphenyl)-4,5-dihydro-3(2H)pyridazinone

1 In 100 ml. of dichloroethane were suspended 10 g. of succinic anhydride and 30 g. of aluminum chloride, and to this mixture was added dropwise with stirring 14.2 g. of p-chloro-m-cresol. After completion of the addition, the mixture was stirred for one hour while maintaining the temperature of the reaction vessel at 100° – 120° C. The reaction mixture was then left to cool and added with vigorous stirring to a mixture of 200 g. of water and 40 ml. of conc. hydrochloric acid. The resulting mixture was allowed to stand for a while, and the precipitated solid was collected by filtration. This solid was repeatedly washed with water until the dropping washing became neutral. The solid was then dried and recrystallized from methanol to give 9.7 g. of 4-(5-chloro-2-hydroxy-4-methylphenyl)-4-oxobutyric acid of m.p. 181° – 182° C. (Yield 40%).

②To 70 ml. of ethanol was added 7 g. of 4-(5-chloro-2-hydroxy-4-methylphenyl)-4-oxobutyric acid, and a solution was made by heating to about 50° C. This solution was then treated in the manner as in Example 1 — ② to give 2.4 g. of 6-(5-chloro-2-hydroxy-4-methylphenyl)-4,5-dihydro-3(2H)pyridazinone of m.p. above 300° C.

Following the procedures as described in the above-mentioned Example 3-①, there were produced the following compounds, 4-(3,5-dichloro-2-hydroxyphenyl)-4-oxobutyric acid, m.p. 166° – 167° C.

4-(4-chloro-2-hydroxyphenyl)-4-oxobutyric acid, m.p. 180° – 181° C.

4-(5-chloro-2-hydroxyphenyl)-4-oxobutyric acid, m.p. 181° – 182° C.

4-(3-chloro-4-methoxyphenyl)-4-oxobutyric acid, m.p. 192° – 198° C.

4-(3,4-dichlorophenyl)-4-oxobutyric acid, m.p. 170° – 173° C.

EXAMPLE 4

6-(3-bromo-5-chloro-4-methylphenyl)-3(2H)pyridazinone

①In 20 ml. of dichloroethane was suspended 8 g. of aluminum chloride, and to this suspension was added little by little with stirring at room temperature 4.5 g. of 4-(3-chloro-4-methylphenyl)-4-oxobutyric acid. Further, a mixture of 4.2 g. of bromine and 5 ml. of dichloroethane was added dropwise at room temperature during one hour to the stirred reaction mixture. The resulting mixture was stirred for another 6 hours, allowed to stand overnight and added to a mixture of 150 g. of ice and 25 ml. of conc. hydrochloric acid. This was then extracted with 300 ml. of ethyl acetate, and the extract was repeatedly washed with water and dried over anhydrous sodium sulfate. Upon evaporation of the solvent, there was obtained 5.95 g. of a residue. To the residue was added 35 ml of toluene, and the mixture was stirred at 60° C. for one hour and allowed to stand overnight. The produced crystals were collected by filtration to give 3.9 g. of 4-(3-bromo-5-chloro-4-methylphenyl)-4-oxobutyric acid of m.p. 183° – 185° C.

②To 100 ml. of ethanol was added with heating 10 g. of 4-(3-bromo-5-chloro-4-methylphenyl)-4-oxobutyric acid to make a solution. To the solution was added dropwise with stirring at about 50° C. 1.8 g. of hydrazine hydrate. After completion of the addition, the reaction mixture was treated in the manner as in Example 1-② to give 7.4 g. of 6-(3-bromo-5-chloro-4-methylphenyl)-4,5-dihydro-3(2H)pyridazinone of m.p. 199° – 200° C.

③In acetic acid heated to 70° C. was suspended 6.3 g. of 6-(3-bromo-5-chloro-4-methylphenyl)-4,5-dihydro-3(2H)pyridazinone, and to this suspension was added dropwise with stirring 3.7 g. of bromine. After completion of the addition, the reaction mixture was treated in the manner as in Example 1-③ to give 6.2 g. of the desired product of m.p. 247° – 250° C.

EXAMPLE 5

6-(3,5-dichloro-4-hydroxyphenyl)-3(2H)pyridazinone

①In 110 ml. of dichloroethane was suspended 32 g. of aluminum chloride, and to this suspension was added little by little with stirring at room temperature 21 g. of 4-(4-methoxyphenyl)-4-oxobutyric acid. Into this mixture was introduced at 40° C. during 2 hours 43 g. of chlorine gas, and this mixture was stirred at room temperature for 3 hours. After completion of the reaction, the reaction mixture was treated in the manner as in Example 4 - ① to give 15.6 g. of 4-(3,5-dichloro-4-hydroxyphenyl)-4-oxobutyric acid of m.p. 180° – 183° C.

②To 20 ml. of ethanol was added 1.65 g. of 4-(3,5-dichloro-4-hydroxyphenyl)-4-oxobutyric acid, and the mixture was heated at about 50° C. to dissolve. To the stirred solution was added dropwise 0.34 g. of hydrazine hydrate. After completion of the additions, this was treated in the manner as in Example 1-② to give 1.0 g. of 6-(3,5-dichloro-4-hydroxyphenyl)-4,5-dihydro-3(2H)-pyridazinone of m.p. 257° – 263° C.

③In acetic acid heated to 70° C. was suspended 4.3 g. of 6-(3,5-dichloro-4-hydroxyphenyl)-4,5-dihydro-3(2H)pyridazinone. The resulting suspension was then treated in the manner as in Example 1-③ to give 3.7 g. of the desired product of m.p. above 300° C.

EXAMPLE 6

6-(3,5-dichloro-4-methoxyphenyl)-3(2H)pyridazinone

①In 300 ml. of absolute ethanol was dissolved 4.7 g. of 4-(3,5-dichloro-4-hydroxyphenyl)-4-oxobutyric acid (prepared in Example 5-①), and into this mixture was introduced under ice-cooling for about 30 minutes gaseous hydrogen chloride.

After completion of the reaction, the solvent was removed by evaporation and the residue was extracted with benzene. The solvent was then removed by evaporation from the extract to leave 5.1 g. of ethyl 4-(3,5-dichloro-4-hydroxyphenyl)-4-oxobutyrate of m.p. 117° – 119° C.

A mixture of 2.9 g. of the so obtained ethyl ester, 7 g. of methyl iodide, 1.4 g. of anhydrous potassium carbonate and 20 ml. of acetone was stirred at 45° – 50° C. for 3 hours. After completion of the reaction, the solvent was removed by evaporation from the reaction mixture and the residue was extracted with benzene. The extract was washed with water. Upon evaporation of the solvent from the extract, there was obtained 2.9 g. of oily ethyl 4-(3,5-dichloro-4-methoxyphenyl)-4-oxobutyrate ($n_D^{28}$ 1.5346). This product was allowed to stand at room temperature to become crystals of m.p. 49° – 52° C.

②A mixture of 2.45 g. of ethyl 4-(3,5-dichloro-4-methoxyphenyl-4-oxobutyric acid, 0.44 g. of hydrazine hydrate and 25 ml. of ethanol was refluxed with heating for 13 hours. After the reaction mixture was allowed to stand to cool, the precipitated crystals were collected by filtration. There was obtained 1.97 g. of 6-(3,5-dichloro-4-methoxyphenyl)-4,5-dihydro-3(2H)pyridazinone of m.p. 175° – 180° C.

③In acetic acid heated to 70° C. was suspended 1.4 g. of 6-(3,5-dichloro-4-methoxyphenyl)-4,5-dihydro-3(2H)pyridazinone. The resulting suspension was then treated in the manner as in Example 1-③ to give hydrobromide of the desired product of m.p. 245° – 251° C. (dec.) From this hydrobromide was obtained 1.0 g. of the desired product of m.p. 245° – 251° C.

EXAMPLE 7

6-(4-amino-3-bromophenyl)-3(2H)pyridazinone

①To a suspension of 3.9 g. of 4-(4-aminophenyl)-4-oxobutyric acid in 150 ml. of dichloroethane was added dropwise with stirring at room temperature 6.7 g. of bromine, and the resulting mixture was allowed to stand overnight. The precipitate produced was collected by filtration, washed with ethanol and dissolved in ethanol with heating. Upon evaporation of ethanol, there was obtained 3.8 g. of ethyl 4-(4-amino-3-bromophenyl)-4-oxobutyrate of m.p. 184° – 186° C.

②A mixture of 1.6 g. of ethyl 4-(4-amino-3-bromophenyl)-4-oxobutyrate, 5.5 ml. of hydrazine hydrate and 100 ml. of ethanol was refluxed with heating for 17 hours. The reaction mixture was then treated in the manner as in Example 1-② to give 0.8 g. of 6-(4-amino-3-bromophenyl)-4,5-dihydro-3(2H)pyridazinone of m.p. 224° C.

③In a mixture of water and isopropanol (20 : 5) was suspended 0.45 g. of 6-(4-amino-3-bromophenyl)-4,5-dihydro-3(2H)pyridazinone, and to the resulting suspension were added 0.45 g. of sodium m-nitrobenzenesulfonate and 0.27 g. of sodium hydroxide. This mixture was then refluxed with heating for 3.5 hours and allowed to stand to cool. The mixture was neutralized with 6 N hydrochloric acid, and the precipitated yellow crystals were collected by filtration. The so obtained crystals were recrystallized from ethanol - acetone to give 0.4 g. of the desired product of m.p. 266° – 267° C.

EXAMPLE 8

6-(4-amino-3,5-dibromophenyl)-3)2H)pyridazinone

To a suspension of 1.2 g. of 6-(4-aminophenyl)-3(2H)pyridazinone in 50 ml. of dichloroethane was added dropwise at room temperature 2.3 g. of bromine. After completion of the addition, the mixture was refluxed with heating for 14 hours. After standing to cool, the reaction mixture was evaporated under reduced pressure to remove the solvent. The so obtained residue was recrystallized from ethanol to give 1.9 g. of the desired product of m.p. 276° – 278° C. (Yield 86%).

EXAMPLE 9

6-(4-amino-3-chlorophenyl)-3(2H)pyridazinone

①To a stirred solution of 2.35 g. of 4-(4-acetamidophenyl)-4-oxobutyric acid in 100 ml. of dichloroethane was added at room temperature 5.3 g. of aluminum chloride, and the resulting mixture was stirred at 50° C. for 5 hours. Into this was introduced under ice-cooling 1.56 g. of chlorine gas, and the mixture was then stirred overnight at room temperature. After further introducing 1.56 g. of gaseous chlorine thereinto, the mixture was stirred at 50° – 55° C. for 2 hours. This was then allowed to stand to cool, poured into 600 ml. of ice-water and extracted with ether. The extract was washed with water until the dropping washing became neutral. The extract was then dried over anhydrous sodium sulfate and evaporated to remove the solvent, leaving 0.9 g. of 4-(4-acetamido-3-chlorophenyl)-4-oxobutyric acid of m.p. 168° – 170° C. (Yield 32%).

②A mixture of 1 g. of 4-(4-acetamido-3-chlorophenyl)-4-oxobutyric acid and 40 ml. of 18% aqueous hydrochloric acid solution was refluxed with heating for 1.5 hours. The resulting mixture was allowed to stand to cool and added to an aqueous ammonia whereby the pH of the mixture turned into about 4.5. The precipitated crystals were collected by filtration and taken into a mixture of acetone and ethanol so as to remove the insoluble materials. The solution was evaporated to remove the solvent, and the residue was dissolved in 10 ml of ethanol. This was, after addition of 0.2 ml. of hydrazine hydrate, then stirred at room temperature for 6.5 hours. After completion of the reaction, the precipitated crystals were collected by filtration to yield 0.6 g. of 6-(4-amino-3-chlorophenyl)-4,5-dihydro-3(2H)pyridazinone of m.p. 238° – 239° C.

③In a mixture of water and isopropanol (20 : 5) was suspended 0.34 g. of 6-(4-amino-3-chlorophenyl)-4,5-dihydro-3(2H)pyridazinone. The resulting suspension was then treated in the manner as in Example 7-③ to give 0.18 g. of the desired product of m.p. 280° – 282° C.

EXAMPLE 10

6-(4-allyloxy-3,5-dichlorophenyl)-4,5-dihydro-3(2H)pyridazinone

In 50 ml. of acetone was mixed 5 g. of 6-(3,5-dichloro-4-hydroxyphenyl)-4,5-dihydro-3(2H)-pyridazinone obtained in Example 5 and 3.3 g. of anhydrous potassium carbonate and to the resulting mixture was added dropwise 2.4 g. of allyl bromide at room temperature while stirring. After completion of the addition, the mixture was heated under reflux for 4 hours. After cooling, the reaction mixture was filtered, the filtrate was concentrated under reduced pressure and the residue was recrystallized from ethanol to give 5.3 g. of the desired product of m.p. 137° C. (Yield 93%).

Following the procedures as described in the above Example 10, there were produced the following compounds.

6-[3,5-dichloro-4-(2propynyloxy)phenyl]-4,5-dihydro-3(2H)pyridazinone, m.p. 198° – 201° C.

6-(3,5-dichloro-4-n-propoxyphenyl)-4,5-dihydro-3(2H)pyridazinone, m.p. 149° – 151° C.

EXAMPLE 11

6-(4-allyloxy-3,5-dichlorophenyl)-3(2H)pyridazinone

To a mixture of 4.9 g. of 6-(3,5-dichloro-4-hydroxyphenyl)-3-(2H)pyridazinone obtained in Example 5 and 2 g. of triethylamine in 30 ml. of dimethylformamide was added dropwise 2.4 g. of allyl bromide at 50° C. while stirring. The mixture was stirred at 50° C. for further 5 hours. After cooling, the reaction mixture was poured into 200 ml. of water and allowed to stand for a while. White solid substance thus formed was recovered by filtration, washed with water, dried to give 3.6 g. of crude crystalline substance, which was then recrystallized from methanol to give 3.2 g. of the desired product as colorless needles of m.p. 214° – 215° C.

Following the procedures as described in Example 11, the following compound was produced.

6-[3,5-dichloro-4-(2-propynyloxy)phenyl]-3(2H)-pyridazinone, m.p. 240° C.

EXAMPLE 12

6-(2-acetoxy-3,5-dibromo-4-methylphenyl)-3(2H)pyridazinone

A mixture of 1.0 g. of 6-(3,5-dibromo-2-hydroxy-4-methylphenyl-3-(2H)pyridazinone and 2 ml. of acetic anhydride in 10 ml. of benzene was heated under reflux for 3 hours. After cooling, the so separated crystalline substance was recovered by filtration and dried to give 0.8 g. of the desired product as yellow needles of m.p. 220° C. (Yield 71.5%).

Following the procedures as described in Example 12, the following compound was produced.

6-(2-acetoxy-3-bromo-5-chloro-4-methylphenyl)-3(2H)pyridazinone, m.p. 215° – 220° C.

EXAMPLE 13

6-(3,5-dichloro-4-p-toluenesulfonyloxyphenyl)-4,5-dihydro-3(2H)pyridazinone

A mixture of 10 g. of 6-(3,5-dichloro-4-hydroxyphenyl)-4,5-dihydro-3(2H)pyridazinone, 7.6 g. of p-toluenesulfonic chloride, 4 g. of triethylamine and 50 ml. of dimethylformamide was stirred at 50° C. for 8 hours. Then, the reaction mixture was treated in the same manner as in Example 11 and recrystallized from dioxane-petroleum ether to give 3.8 g. of the desired product as prisms of m.p. 208° – 209° C.

Following the procedures as described in Example 13, there were produced the following compounds.
  6-(3,5-dichloro-4-p-toluenesulfonyloxyphenyl)-3(2H)pyridazinone, m.p. 254° – 256° C.
  6-(4-acetoxy-3,5-dichlorophenyl)-3(2H)pyridazinone, m.p. 258° – 260° C.

EXAMPLE 14

6-(3,4-dichlorophenyl)-3(2H)pyridazinone potassium salt

To a solution of 0.22 g. of potassium hydroxide in 5 ml. of methanol was added 0.96 g. of 6-(3,4-dichlorophenyl)-3(2H)pyridazinone and the resulting mixture was stirred at room temperature for about 30 minutes. After completion of the reaction, a small amount of insolubles was filtered off and the filtrate was concentrated. A small amount of ethanol was added to the residue and the mixture was again concentrated to dryness. This procedure was repeated twice to give the desired product in its hydrate form as a colorless solid having a melting point of above 280° C.

Following the procedures as described in the above-mentioned Example 14, there were produced the following compounds.
  6-(3,5-dichloro-4-methylphenyl)-3(2H)pyridazinone potassium salt, m.p. above 280° C.
  6-(3,5-dichloro-4-ethylphenyl)-3(2H)pyridazinone potassium salt, m.p. above 280° C.
  6-(3,5-dichloro-4-methoxyphenyl)-3(2H)pyridazinone potassium salt, m.p. above 280° C.

EXAMPLE 15

6-(3,4-dichlorophenyl)-3(2H)pyridazinone calcium salt

To a solution of 0.1 g. of calcium chloride in 5 ml. of water was added 0.5 g. of 6-(3,4-dichlorophenyl)-3(2H)pyridazinone potassium salt and the resulting mixture was stirred at room temperature for about 30 minutes. After completion of the reaction, the so obtained solid product was recovered by filtration, washed with water and then dried to give the desired product in its hydrate form having a melting point of above 280° C.

Following the procedures as described in the above-mentioned Example 15, there were produced the following compounds.
  6-(3,5-dichloro-4-methylphenyl)-3(2H)pyridazinone calcium salt, m.p. above 280° C.
  6-(3,5-dichloro-4-ethylphenyl)-3(2H)pyridazinone calcium salt, m.p. above 280° C.
  6-(3-chloro-4-isopropylphenyl)-3(2H)pyridazinone calcium salt, m.p. above 280° C.
  6-(3,5-dichloro-4-methoxyphenyl)-3(2H)pyridazinone calcium salt, m.p. above 280° C.

EXAMPLE 16

6-(3,5-dichloro-4-methylphenyl)-3(2H)pyridazinone sodium salt

To a solution of 0.16 g. of sodium hydroxide in 5 ml. of methanol was added 1 g. of 6-(3,5-dichloro-4-methylphenyl)-3(2H)pyridazinone and the resulting mixture was stirred at room temperature for about 30 minutes. After completion of the reaction, the reaction mixture was treated and purified in the same manner as in Example 14 to give the desired product in its hydrate form as a colorless solid having a melting point of above 280° C.

Following the procedures as described in the above-mentioned Example 16, there was produced the following compound.
  6-(3,5-dichloro-4-methoxyphenyl)-3(2H)pyridazinone sodium salt, m.p. above 280° C.

EXAMPLE 17

6-(3,5-dichloro-4-methylphenyl)-3(2H)pyridazinone methyl isocyanate

To a hot solution of 1.0 g. of 6-(3,5-dichloro-4-methylphenyl)-3(2H)pyridazinone in 25 ml. of dioxane was added an excess molar amount (above 0.5 ml.) of methyl isocyanate and the mixture in a sealed vessel was allowed to stand at room temperature for 3 hours. Then, 5 ml. of n-hexane was added and the resulting mixture was cooled to give 1.0 g. of the desired product as needles of m.p. ca. 250° C. (with decomp.) (Yield 82%).

Following the procedures as described in Example 17, there were produced the following compounds.
  6-(3,4-dichlorophenyl)-3(2H)pyridazinone methyl isocyanate, m.p. ca. 263° – 264° C. (with decomp.)
  6-(3-chloro-4-methylphenyl)-3(2H)pyridazinone methyl isocyanate, m.p. ca. 270° C. (with decomp.)
  6-(3-bromo-4-methylphenyl)-3(2H)pyridazinone methyl isocyanate, m.p. ca. 270° C. (with decomp.)
  6-(3,5-dichloro-4-hydroxyphenyl)-3(2H)pyridazinone methyl isocyanate, m.p. above 300° C. (with decomp.)

EXAMPLES OF COMPOSITIONS

Examples of the agricultural fungicidal compositions of this invention are given below. All parts are given by weight unless otherwise stated.

EXAMPLE 18 DUSTS

Five parts of compound No. 34, 50 parts of talc and 45 parts of kaolin were uniformly mixed to form a dusts.

EXAMPLE 19 WETTABLE POWDERS

Fifty parts of compound No. 7, 29 parts of clay, 10 parts of diatomaceous earth, 5 parts of white carbon, 3 parts of sodium lignosulfonate, 2 parts of "Newcoal" 1106 (trade name, Nihon Nyukazai K.K., Japan) and 1 part of polyvinyl alcohol were uniformly mixed in a mixer and pulverized three times by a hammer mill to give a wettable powder.

EXAMPLE 20 GRANULES

Seventy parts of Compound No. 1 was finely pulverized and 30 parts of clay were added thereto and then mixed in a mixer to form a premixture. 10 Parts of the premix were uniformly mixed with 60 parts of clay and 30 parts of bentonite in a mixer. The resulting mixture was kneaded with a suitable amount of water in a kneader, extruded through a screen having a diameter of 0.8 mm and dried in a draft drier at 50° C. The product thus formed was adjusted by a sifter to form granules.

Experimental examples of the present fungicidal compositions thus prepared are given below. The wettable powders prepared according to the procedures in the above-mentioned Example 19 are used in the following experiments, each containing 50% by weight of an active compound of this invention.

EXPERIMENT 1

Test on preventive and curative effect against damping-off on cucumber

Pathogenic fungus of damping-off (Rhizoctonia solani) was incubated on rice bran at 28° C. for 2 weeks and homogeneously mixed with soil. The soil was placed in a pot having a diameter of 12 cm. and 20 seeds of cucumber (variety: Sagamihanpaku) were sowed thereon. Then, each test preparation at 25 ppm was poured thereonto at a rate of 3 l./m². Pots were kept in a greenhouse at 25° C. for 2 weeks, after which infected seedlings (number) were investigated. The results are summarized in Table 1.

Table 1

| Compd. No. | Infected seedlings (number) | Compd. No. | Infected seedlings (number) |
| --- | --- | --- | --- |
| 1 | 3 | 32 | 3 |
| hydrobromide of 1 | 3 | 33 | 12 |
| potassium salt of 1 | 2 | 34 | 0 |
| calcium salt of 1 | 2 | hydrobromide of 34 | 0 |
| 4 | 7 | potassium salt of 34 | 1 |
| 5 | 5 | sodium salt of 34 | 0 |
| hydrobromide of 5 | 6 | calcium salt of 34 | 0 |
| 6 | 5 | 35 | 13 |
| 7 | 0 | 36 | 8 |
| hydrobromide of 7 | 0 | 37 | 6 |
| potassium salt of 7 | 0 | 39 | 10 |
| sodium salt of 7 | 0 | mixture of 4 and 7 (1:1) | 2 |
| calcium salt of 7 | 0 | 62 | 4 |
| 8 | 2 | 87 | 10 |
| 10 | 3 | 90 | 14 |
| potassium salt of 10 | 4 | 91 | 6 |
| calcium salt of 10 | 5 | 92 | 9 |
| 12 | 13 | 94 | 6 |
| 20 | 4 | 96 | 10 |
| 21 | 0 | 115 | 13 |
| 22 | 12 | 116 | 6 |
| 25 | 13 | 117 | 5 |
| 26 | 12 | 118 | 15 |
| 28 | 15 | 120 | 14 |
| 29 | 7 | 129 | 10 |
| 30 | 4 | 139 | 17 |
| 31 | 11 | Untreated control | 59 |

EXPERIMENT 2

Test on controlling effect against sheath blight in rice plants (preventive effect)

Rice plant seedlings (variety: Koganenishiki) at 4 – 5 leaf stage were sprayed with each test preparation at 30 ppm in a total amount of 50 ml. per 3 pots. Host plants were left at room temperature for 24 hours and then 4 – 5 oat grains, on which pathogenic fungus of sheath blight (Pellicularia sasakii) was previously incubated, were placed around the root of rice plant. Host plants were placed in a greenhouse at 25° – 27° C. and after 10 days from the inoculation a damage degree was investigated by determining a height of the diseased spot (cm.). The results are shown in Table 2.

Table 2

| Compd. No. | Height of diseased spot (cm.) | Compd. No. | Height of diseased spot (cm.) |
| --- | --- | --- | --- |
| 1 | 0.5 | 35 | 2.0 |
| hydrobromide of 1 | 0.4 | 36 | 2.3 |
| potassium salt of 1 | 0.5 | 37 | 1.2 |
| calcium salt of 1 | 0.4 | 39 | 0.7 |
| 2 | 0.5 | mixture of 4 and 7 (1:1) | 0.9 |
| 4 | 1.2 | | |
| 5 | 0.4 | 87 | 0.9 |
| hydrobromide of 5 | 0.6 | 90 | 1.5 |
| 6 | 0.9 | 91 | 1.2 |
| 7 | 0 | 92 | 1.7 |
| hydrobromide of 7 | 0 | 93 | 0.4 |
| potassium salt of 7 | 0 | 94 | 0.8 |
| sodium salt of 7 | 0 | 96 | 2.0 |
| calcium salt of 7 | 0 | 116 | 0.8 |
| 8 | 0 | 117 | 1.7 |
| 10 | 0.4 | 118 | 1.9 |
| potassium salt of 10 | 0.5 | 120 | 0.2 |
| calcium salt of 10 | 0.9 | 128 | 2.0 |
| 20 | 0.6 | 129 | 3.1 |
| 21 | 0.1 | 139 | 3.0 |
| 22 | 2.9 | 146 | 1.9 |
| 26 | 1.9 | 61 | 0.9 |
| 28 | 0.5 | 62 | 0.2 |
| 29 | 1.8 | 63 | 0.8 |
| 30 | 0 | 64 | 0.7 |
| 31 | 1.3 | 52 | 0.6 |
| 32 | 1.3 | 66 | 0.1 |
| 33 | 1.6 | 67 | 0.1 |
| 34 | 0 | 68 | 0.7 |
| hydrobromide of 34 | 0 | 69 | 0.7 |
| potassium salt of 34 | 0 | 70 | 2.1 |
| sodium salt of 34 | 0.2 | 71 | 2.5 |
| calcium salt of 34 | 0 | 88 | 2.0 |
| | | Untreated control | 14.2 |

EXPERIMENT 3

Test on controlling effect against sheath blight in rice plants (curative effect)

Rice plant seedlings (variety: Koganenishiki at 6 – 7 leaf stage were infected with sheath blight by placing around the root thereof 4 – 5 oat grains, on which pathogenic fungus (Pellicularia sasakii) was previously incubated. Host plants were placed in a greenhouse at 25° – 27° C. After 3 days from the inoculation (at that time a height of diseased spot was 1.8 – 2.0 cm.), host plants were taken out from the greenhouse and sprayed with each test preparation at 100 ppm in a total amount of 50 ml. per 3 pots. After air-drying, plants were again placed in a greenhouse at 25° – 27° C. After 10 days from the application, a diseased degree was investigated by determining the height of a diseased spot (cm.). The results are shown in Table 3.

Table 3

| Compd. No. | Height of diseased spot (cm.) | Compd. No. | Height of diseased spot (cm.) |
| --- | --- | --- | --- |
| 1 | 0.9 | 32 | 3.2 |
| hydrobromide of 1 | 1.0 | 33 | 3.1 |
| potassium salt of 1 | 1.0 | 34 | 0.5 |
| calcium salt of 1 | 1.2 | hydrobromide of 34 | 0.5 |
| 4 | 2.3 | potassium salt of 34 | 0.6 |
| 5 | 1.0 | sodium salt of 34 | 0.6 |
| hydrobromide of 5 | 1.2 | calcium salt of 34 | 0.6 |
| 6 | 1.9 | 35 | 4.1 |
| 7 | 0.3 | 36 | 4.2 |
| hydrobromide of 7 | 0.3 | 37 | 1.9 |
| potassium salt of 7 | 0.4 | 39 | 0.9 |
| sodium salt of 7 | 0.4 | mixture of 4 and 7 (1:1) | 1.5 |
| calcium salt of 7 | 0.4 | 87 | 1.4 |
| 8 | 0.3 | 90 | 2.9 |
| 10 | 1.2 | 91 | 2.3 |
| potassium salt of 10 | 1.2 | 92 | 3.1 |
| calcium salt of 10 | 1.3 | 93 | 0.8 |

Table 3-continued

| Compd. No. | Height of diseased spot (cm.) | Compd. No. | Height of diseased spot (cm.) |
|---|---|---|---|
| 20 | 1.7 | 94 | 1.2 |
| 21 | 1.8 | 96 | 3.5 |
| 22 | 4.1 | 116 | 1.5 |
| 26 | 2.2 | 117 | 3.0 |
| 28 | 1.0 | 118 | 3.2 |
| 29 | 2.4 | 120 | 0.9 |
| 30 | 0.3 | 128 | 3.5 |
| 31 | 2.9 | 146 | 3.1 |
| | | Untreated control | 15.6 |

EXPERIMENT 4

Test on preventive and curative effect against sheath blight in rice plants (curative effect)

Rice plant seedlings (variety: Koganenishiki) at 4 – 5 leaf stage were infected with sheath blight by placing around the root thereof 4 – 5 oat grains, on which pathogenic fungus (Pellicularia sasakii) was previously incubated. Host plants were placed in a greenhouse at 25° – 27° C. After 2 days from the inoculation (at that time a height of diseased spot was 1.8 – 2.0 cm.), host plants were taken out from the greenhouse and sprayed with each test preparation at 100 ppm in a total amount of 50 ml. per 3 pots. After air-drying, plants were again placed in a greenhouse at 25° – 27° C. After 8 days from the application, a diseased degree was investigated by determining the height of a diseased spot (cm.). The results are shown in Table 4.

Table 4

| Compd. No. | Height of deseased spot (cm.) | Compd. No. | Height of diseased spot (cm.) |
|---|---|---|---|
| 1 | 1.9 | sodium salt of 7 | 2.1 |
| hydrobromide of 1 | 2.0 | calcium salt of 7 | 2.2 |
| potassium salt of 1 | 2.1 | 10 | 2.0 |
| calcium salt of 1 | 2.5 | potassium salt of 10 | 1.9 |
| 4 | 4.2 | calcium salt of 10 | 1.9 |
| 6 | 3.7 | 20 | 2.1 |
| 7 | 1.9 | 21 | 2.2 |
| hydrobromide of 7 | 1.9 | Untreated control | 11.7 |
| potassium salt of 7 | 2.0 | | |

It will be apparent from the above results that the pyridazinone compounds in this invention have remarkably high fungicidal activities against various pathogenic fungi.

What is claimed is:

1. An agricultural fungicidal composition which comprises as an active ingredient a compound having the formula

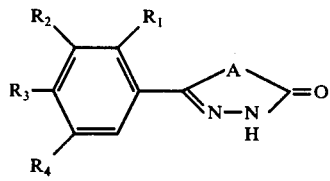

wherein
$R_1$ is hydrogen atom, hydroxy group, a group of the formula -O-CO-$R_5$ in which $R_5$ is an alkyl group of 1 – 5 carbon atoms or a group of the formula -O-SO$_2$-$R_6$ in which $R_6$ is a phenyl group optionally substituted with a halogen atom or an alkyl group of 1 – 3 carbon atoms;
$R_2$ and $R_4$ may be the same or different and each represents halogen atom or one of $R_2$ and $R_4$ is a halogen atom and the other is hydrogen atom;
$R_3$ is hydrogen atom, an alkyl group of 1 – 6 carbon atoms, an alkoxy group of 1 – 6 carbon atoms, an alkenyloxy group of 3 – 5 carbon atoms, an alkynyloxy group of 3 – 4 carbon atoms, amino group, hydroxy group, a halogen atom, a group of the formula -O-CO-$R_5$ in which $R_5$ is as defined above or a group of the formula -O-SO$_2$-$R_6$ in which $R_6$ is as defined above; and
A is a group -CH$_2$-CH$_2$- or -CH=CH- or a salt thereof where A is the group -CH=CH- and an agriculturally acceptable carrier.

2. The composition according to claim 1 wherein $R_1$ is hydrogen atom or hydroxy group, $R_2$ and $R_4$ may be the same or different and each represents chlorine atom, fluorine atom or bromine atom and $R_3$ is hydrogen atom, an alkyl group of 1 or 2 carbon atoms, amino group, an alkoxy group of 1 or 2 carbon atoms, or an alkenyloxy group of 3 or 4 carbon atoms.

3. The composition according to claim 1 wherein $R_1$ and $R_4$ are hydrogen atom; and $R_2$ and $R_3$ may be the same or different and each represents chlorine atom, fluorine atom or bromine atom or $R_2$ is chlorine atom or bromine atom and $R_3$ is hydrogen atom or an alkyl group of 1 or 2 carbon atoms.

4. The composition according to claim 1 wherein $R_1$ is hydrogen atom, $R_2$ and $R_4$ may be the same or different and each represents chlorine atom, fluorine atom or bromine atom and $R_3$ is an alkyl group of 1 or 2 carbon atoms or an alkoxy group of 1 or 2 carbon atoms.

5. The composition according to claim 1 wherein said compound is selected from the group consisting of
6-(3,4-dichlorophenyl)-3(2H)pyridazinone,
6-(3-chloro-4-methylphenyl)-3(2H)pyridazinone,
6-(3-bromo-4-methylphenyl)-3(2H)pyridazinone,
6-(3-chloro-4-isopropylphenyl)-3(2H)pyridazinone,
6-(3,5-dichloro-4-methylphenyl)-3(2H)pyridazinone,
6-(3,5-dibromo-4-methylphenyl)-3(2H)pyridazinone,
6-(3,5-dichloro-4-ethylphenyl)-3(2H)pyridazinone,
6-(3,5-dibromo-4-chloro-2-hydroxyphenyl)-3(2H)pyridazinone,
6-(3,5-dibromo-4-methyl-2-hydroxyphenyl)-33(2H)pyridazinone,
6-(3-bromo-5-chloro-4-methyl-2-hydroxyphenyl)-3(2H)pyridazinone,
6-(3-bromo-5-chloro-4-methylphenyl)-3(2H)pyridazinone,
6-(3-bromophenyl)-3(2H)pyridazinone,
6-(3-chlorophenyl)-3(2H)pyridazinone,
6-(3,5-dichloro-4-methoxyphenyl)-3(2H)pyridazinone,
6-(3,5-dibromo-4-aminophenyl)-3(2H)pyridazinone,
6-(3-chloro-4-fluorophenyl)-3(2H)pyridazinone,
6-(3,4-dichlorophenyl)-3(2H)pyridazinone methylisocyanate,
6-(3,5-dichloro-4-methylphenyl)-3(2H)pyridazinone methylisocyanate,
6-(3,4-dichlorophenyl)-4,5-dihydro-3(2H)pyridazinone,
6-(3-bromophenyl)-4,5-dihydro-3(2H)pyridazinone,
6-(3,5-dichloro-4-methoxyphenyl)-4,5-dihydro-3(2H)pyridazinone,
6-(3,4,5-trichlorophenyl)-3(2H)pyridazinone,
6-(3,4-dibromophenyl)-3(2H)pyridazinone, 6-(3-bromo-4-chlorophenyl)-3(2H)pyridazinone,
6-(3-bromo-4-fluorophenyl)-3(2H)pyridazinone,
6-(3-chloro-4-methylphenyl)-3(2H)pyridazinone methylisocyanate and
6-(3-bromo-4-methyl-5-chlorophenyl)-3(2H)pyridazinone methylisocyanate.

6. The composition according to claim 1 wherein said compound is contained in an amount of 0.1 - 99% by weight, based upon the composition.

7. A method for combatting pathogenic fungi in plants, seeds and soils which comprises applying to said subjects a fungicidal amount of a compound having the formula

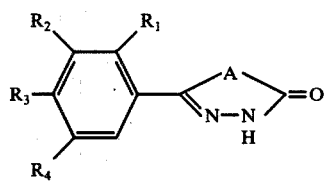

wherein
R$_1$ is hydrogen atom, hydroxy group, a group of the formula -O-CO-R$_5$ in which R$_5$ is an alkyl group of 1 - 5 carbon atoms or a group of the formula -O-SO$_2$-R$_6$ in which R$_6$ is a phenyl group optionally substituted with halogen or an alkyl group of 1 - 3 carbon atoms;
R$_2$ and R$_4$ may be the same or different and each represents a halogen atom or one of R$_2$ and R$_4$ is a halogen atom and the other is hydrogen atom;
R$_3$ is hydrogen atom, an alkyl group of 1 - 6 carbon atoms, an alkoxy group of 1 - 6 carbon atoms, an alkenyloxy group of 3 - 5 carbon atoms, an alkynyloxy group of 3 - 4 carbon atoms, amino group, hydroxy group, a halogen atom, a group of the formula -O-CO-R$_5$ in which R$_5$ is as defined above or a group of the formula -O-SO$_2$-R$_6$ in which R$_6$ is as defined above; and
A is a group -CH$_2$-CH$_2$- or -CH=CH- or a salt thereof where A is the group -CH=CH-.

8. The method according to claim 7 wherein R$_1$ is hydrogen atom or hydroxy group, R$_2$ and R$_4$ may be the same or different and each represents chlorine atom, fluorine atom or bromine atom and R$_3$ is hydrogen atom, an alkyl group of 1 or 2 carbon atoms, amino group, an alkoxy group of 1 or 2 carbon atoms, or an alkenyloxy group of 3 or 4 carbon atoms.

9. The method according to claim 7 wherein R$_1$ and R$_4$ are hydrogen atom; and R$_2$ and R$_3$ may be the same or different and each represents chlorine atom, fluorine atom or bromine atom or R$_2$ is chlorine atom or bromine atom and R$_3$ is hydrogen atom or an alkyl group of 1 or 2 carbon atoms.

10. The method according to claim 7 wherein R$_1$ is hydrogen atom, R$_2$ and R$_4$ may be the same or different and each represents chlorine atom, fluorine atom or bromine atom and R$_3$ is an alkyl group of 1 or 2 carbon atoms or an alkoxy group of 1 or 2 carbon atoms.

11. The method according to claim 7 wherein said compound is selected from the group consisting of
6-(3,4-dichlorophenyl)-3(2H)pyridazinone,
6-(3-chloro-4-methylphenyl)-3(2H)pyridazinone,
6-(3-bromo-4-methylphenyl)-3(2H)pyridazinone,
6-(3-chloro-4-isopropylphenyl)-3(2H)pyridazinone,
6-(3,5-dichloro-4-methylphenyl)-3(2H)pyridazinone,
6-(3,5-dibromo-4-methylphenyl)-3(2H)pyridazinone,
6-(3,5-dichloro-4-ethylphenyl)-3(2H)pyridazinone,
6-(3,5-dibromo-4-chloro-2-hydroxyphenyl)-3(2H)pyridazinone,
6-(3,5-dibromo-4-methyl-2-hydroxyphenyl)-3(2H)pyridazinone,
6-(3-bromo-5-chloro-4-methyl-2-hydroxyphenyl)-3(2H)pyridazinone,
6-(3-bromo-5-chloro-4-methylphenyl)-3(2H)pyridazinone,
6-(3-bromophenyl)-3(2H)pyridazinone,
6-(3-chlorophenyl)-3(2H)pyridazinone,
6-(3,5-dichloro-4-methoxyphenyl)-3(2H)pyridazinone,
6-(3,5-dibromo-4-aminophenyl)-3(2H)pyridazinone,
6-(3-chloro-4-fluorophenyl)-3(2H)pyridazinone,
6-(3,4-dichlorophenyl)-3(2H)pyridazinone methylisocyanate,
6-(3,5-dichloro-4-methylphenyl)-3(2H)pyridazinone methylisocyanate,
6-(3,4-dichlorophenyl)-4,5-dihydro-3(2H)pyridazinone,
6-(3-bromophenyl)-4,5-dihydro-3(2H)pyridazinone,
6-(3,5-dichloro-4-methoxyphenyl)-4,5-dihydro-3(2H)pyridazinone,
6-(3,4,5-trichlorophenyl)-3(2H)pyridazinone,
6-(3,4-dibromophenyl)-3(2H)pyridazinone,
6-(3-bromo-4-chlorophenyl)-3(2H)pyridazinone,
6-(3-bromo-4-fluorophenyl)-3(2H)pyridazinone,
6-(3-chloro-4-methylphenyl)-3(2H)pyridazinone methylisocyanate and
6-(3-bromo-4-methyl-5-chlorophenyl)-3(2H)pyridazinone methylisocyanate.

12. 6-(3,5-Dibromo-4-aminophenyl)-3(2H)pyridazinone.

13. 6-(3,5-Dichloro-4-methylphenyl)-3(2H)pyridazinone methylisocyanate.

14. 6-(3-Bromo-4-methylphenyl)-3(2H)pyridazinone.

15. 6-(3-Chloro-4-isopropylphenyl)-3(2H)pyridazinone.

16. 6-(3,5-Dichloro-4-methylphenyl)-3(2H)pyridazinone.

17. 6-(3,5-Dibromo-4-methylphenyl)-3(2H)pyridazinone.

18. 6-(3,5-Dichloro-4-ethylphenyl)-3(2H)pyridazinone.

19. 6-(3,5-Dibromo-4-chloro-2-hydroxyphenyl)-3(2H)pyridazinone.

20. 6-(3,5-Dibromo-4-methyl-2-hydroxyphenyl)-3(2H)pyridazinone.

21. 6-(3-Bromo-5-chloro-4-methyl-2-hydroxyphenyl)-3(2H)pyridazinone.

22. 6-(3-Bromo-5-chloro-4-methylphenyl)-3(2H)pyridazinone.

23. 6-(3-Bromophenyl)-3(2H)pyridazinone.

24. 6-(3,5-Dichloro-4-methoxyphenyl)-3(2H)pyridazinone.

* * * * *

UNITED STATES PATENT OFFICE
CERTIFICATE OF CORRECTION

Patent No. 4,052,395         Dated October 4, 1977

Inventor(s) TERUOMI JOJIMA et al

It is certified that error appears in the above-identified patent and that said Letters Patent are hereby corrected as shown below:

Column 2, line 35, in the formula: replace "-O-" with --- $-O^-$ ---.

Column 21, line 55: delete "$-CO-R_5$ or".

Column 29, line 26: rewrite "entioned" as ---mentioned---.

Column 29, line 27: rewrite "llowing" as ---following---.

Column 29, line 38: replace "-3(2)" with --- -3(2H) ---.

Column 30, line 50: replace "6-(5chloro-" with --- 6-(5-chloro- ---.

UNITED STATES PATENT OFFICE
CERTIFICATE OF CORRECTION

Patent No. 4,052,395    Dated  October 4, 1977

Inventor(s)  TERUOMI JOJIMA et al

It is certified that error appears in the above-identified patent and that said Letters Patent are hereby corrected as shown below:

Column 34, line 59: after "methylphenyl", insert ---)---.

Column 40, line 47: replace "33" with ---3---.

Signed and Sealed this

Eighth Day of August 1978

[SEAL]

Attest:

RUTH C. MASON
Attesting Officer

DONALD W. BANNER
Commissioner of Patents and Trademarks